(12) United States Patent
Creton

(10) Patent No.: US 11,905,541 B2
(45) Date of Patent: *Feb. 20, 2024

(54) EFFICIENT PRODUCT CLEAVAGE IN TEMPLATE-FREE ENZYMATIC SYNTHESIS OF POLYNUCLEOTIDES

(71) Applicant: DNA Script SAS, Le Kremlin-Bicêtre (FR)

(72) Inventor: Sandrine Creton, Le Kremlin-Bicêtre (FR)

(73) Assignee: DNA Script SAS, Le Kremlin-Bicêtre (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/837,660

(22) Filed: Jun. 10, 2022

(65) Prior Publication Data

US 2023/0105977 A1 Apr. 6, 2023

Related U.S. Application Data

(63) Continuation of application No. 16/981,595, filed as application No. PCT/EP2020/053417 on Feb. 11, 2020, now Pat. No. 11,359,221.

(30) Foreign Application Priority Data

Feb. 12, 2019 (EP) .................................... 19305174

(51) Int. Cl.
| | |
|---|---|
| *C12P 19/34* | (2006.01) |
| *C12P 19/38* | (2006.01) |
| *C12Q 1/68* | (2018.01) |
| *C12N 9/12* | (2006.01) |
| *C12Q 1/6806* | (2018.01) |
| *C12Q 1/6876* | (2018.01) |
| *C12N 15/10* | (2006.01) |
| *C12P 19/14* | (2006.01) |

(52) U.S. Cl.
CPC .............. *C12P 19/14* (2013.01); *C12P 19/34* (2013.01)

(58) Field of Classification Search
CPC ........ C12P 19/14; C12P 19/34; C12N 15/111; C12N 15/11; C12N 15/1096
See application file for complete search history.

(56) References Cited

U.S. PATENT DOCUMENTS

| | | |
|---|---|---|
| 4,772,691 A | 9/1988 | Herman |
| 5,047,524 A | 9/1991 | Andrus |
| 5,262,530 A | 11/1993 | Andrus |
| 5,367,066 A | 11/1994 | Urdea |
| 5,436,143 A | 7/1995 | Hyman |
| 5,516,664 A | 5/1996 | Hyman |
| 5,602,000 A | 2/1997 | Hyman |
| 5,656,745 A | 8/1997 | Bischofberger |
| 5,700,642 A | 12/1997 | Monforte |
| 5,744,595 A | 4/1998 | Srivastava |
| 5,763,594 A | 6/1998 | Hiatt |
| 5,798,210 A | 8/1998 | Canard |
| 5,808,045 A | 9/1998 | Hiatt |
| 5,872,244 A | 2/1999 | Hiatt |
| 5,917,031 A | 6/1999 | Miura |
| 5,935,527 A | 8/1999 | Andrus |
| 5,990,300 A | 11/1999 | Hiatt |
| 6,214,987 B1 | 4/2001 | Hiatt |
| 6,232,465 B1 | 5/2001 | Hiatt |
| 6,623,929 B1 | 9/2003 | Densham |
| 6,664,079 B2 | 12/2003 | Ju |
| 6,777,189 B2 | 8/2004 | We |
| 7,057,026 B2 | 6/2006 | Barnes |
| 7,078,499 B2 | 7/2006 | Odedra |
| 7,125,671 B2 | 10/2006 | Sood |
| 7,270,951 B1 | 9/2007 | Stemple |
| 7,345,159 B2 | 3/2008 | Ju |
| 7,407,757 B2 | 8/2008 | Brenner |
| 7,494,797 B2 | 2/2009 | Mueller |
| 7,544,794 B1 | 6/2009 | Benner |
| 7,566,537 B2 | 7/2009 | Balasubramanian |
| 7,635,578 B2 | 12/2009 | Ju |
| 7,713,698 B2 | 5/2010 | Ju |
| 7,790,869 B2 | 9/2010 | Balasubramanian |
| 7,932,025 B2 | 4/2011 | Carr |
| 7,939,259 B2 | 5/2011 | Kokoris |
| 8,034,923 B1 | 10/2011 | Benner |
| 8,212,020 B2 | 7/2012 | Benner |
| 8,263,335 B2 | 9/2012 | Carr |
| 8,394,586 B2 | 3/2013 | Balasubramanian |
| 8,674,086 B2 | 3/2014 | Liu |
| 8,808,988 B2 | 8/2014 | Zhao |

(Continued)

FOREIGN PATENT DOCUMENTS

| | | |
|---|---|---|
| EP | 1165786 B1 | 7/2008 |
| EP | 2876166 B1 | 12/2016 |

(Continued)

OTHER PUBLICATIONS

International Search Report dated May 29, 2020 for International Application No. PCT/EP2020/053417. (Submitted in related U.S. Appl. No. 16/981,595).

Written Opinion dated May 29, 2020 for International Application No. PCT/EP2020/053417. (Submitted in related U.S. Appl. No. 16/981,595).

Vik, Erik Sebastian, et al. "Endonuclease V cleaves at inosines in RNA." Nature communications 4.1 (2013): 1-7. (Submitted in related U.S. Appl. No. 16/981,595).

(Continued)

*Primary Examiner* — Maryam Monshipouri
(74) *Attorney, Agent, or Firm* — Gardella Grace P.A.

(57) ABSTRACT

The present invention is directed to methods and kits for template-free enzymatic synthesis of polynucleotides that include or enable a step of efficiently cleaving the polynucleotide products from its initiator using an endonuclease V activity and initiator with a 3'-penultimate deoxyinosine.

15 Claims, 1 Drawing Sheet
Specification includes a Sequence Listing.

(56) References Cited

U.S. PATENT DOCUMENTS

| | | | |
|---|---|---|---|
| 8,808,989 | B1 | 8/2014 | Efcavitch |
| 9,121,062 | B2 | 9/2015 | Balasubramanian |
| 9,388,463 | B2 | 7/2016 | Balasubramanian |
| 9,410,197 | B2 | 8/2016 | Bergmann |
| 9,896,709 | B2 | 2/2018 | Makarov |
| 9,957,549 | B2 | 5/2018 | Armour |
| 10,435,676 | B2 | 10/2019 | Champion |
| 10,752,887 | B2 | 8/2020 | Champion |
| 2011/0171649 | A1 | 7/2011 | Kutyavin |
| 2014/0363851 | A1 | 12/2014 | Efcavitch |
| 2014/0363852 | A1 | 12/2014 | Efcavitch |
| 2018/0016609 | A1 | 1/2018 | Chen |
| 2018/0023108 | A1 | 1/2018 | Chen |
| 2018/0201968 | A1 | 7/2018 | Chen |
| 2019/0144905 | A1 | 5/2019 | Chen |
| 2019/0264248 | A1 | 8/2019 | Ybert |
| 2019/0300923 | A1 | 10/2019 | Ybert |
| 2019/0338331 | A1 | 11/2019 | Chen |
| 2020/0002690 | A1 | 1/2020 | Ybert et al. |
| 2020/0231619 | A1 | 7/2020 | Ybert |
| 2021/0254114 | A1 | 8/2021 | Creton |

FOREIGN PATENT DOCUMENTS

| | | |
|---|---|---|
| WO | WO1991/06678 | 5/1991 |
| WO | WO1996/07669 | 3/1996 |
| WO | WO2004/018497 | 3/2004 |
| WO | WO2005/005667 | 1/2005 |
| WO | WO2005/059096 | 6/2005 |
| WO | WO2015/159023 | 10/2015 |
| WO | WO2016/034807 | 3/2016 |
| WO | 2017/216472 A3 | 12/2017 |
| WO | WO2017/216472 | 12/2017 |
| WO | 2018/134616 A1 | 7/2018 |
| WO | WO2018/134616 | 7/2018 |
| WO | WO2020/020608 | 1/2020 |
| WO | WO2020/043846 | 3/2020 |
| WO | 2020/077227 A2 | 4/2020 |
| WO | WO2020/077227 | 4/2020 |
| WO | WO2020/099451 | 5/2020 |
| WO | WO2020/165137 | 5/2020 |
| WO | WO2020/165137 | 8/2020 |
| WO | WO2020/165334 | 8/2020 |

OTHER PUBLICATIONS

Beabealashvilli et al, "Nucleoside 5'-triphosphates modified at sugar residues as substrates for calf thymus terminal deoxynucleotidyl transferase and for AMV reverse transcriptase," Biochim. Biophys. Acta., 868(2-3): 136-144 (1986).

Becker et al, "The enzymatic cleavage of phosphate termini from polynucleotides," J. Biol. Chem., 242(5): 936-950 (1967).

Cameron et al, "3'-phosphatase activity in T4 polynucleotide kinase," Biochemistry, 16(23): 5120-5126 (1977).

Canard et al, "DNA polymerase fluorescent substrates with reversible 3'-tags," Gene, 148: 1-6 (1994).

Canard et al, "Catalytic editing properties of DNA polymerases," Proc. Natl. Acad. Sci., 92: 10859-10863 (1995).

Chen et al, "The history and advances of reversible terminators used in new generations of sequencing technology," Genomics Proteomics Bioinformatics, 11: 34-40 (2013).

Delarue et al, "Crystal structures of a template-independent DNA polymerase: murine terminal deoxynucleotidyltransferase," Embo J., 21(3): 427-439 (2002).

Ferrero et al, "Chemoenzymatic transformations in nucleoside chemistry," Monatshefte fur Chemie, 131: 585-616 (2000).

Flickinger et al, "Differential incorporation of biotinylated nucleotides by terminal deoxynucleotidyl transferase," Nucleic Acids Research, 20(9): 2382 (1992).

Gates et al, "Endonuclease V of *Escherichia coli*," J. Biol. Chem., 252(5): 1647-1653 (1977).

Gebeyehu et al, "Novel biotinylated nucleotide—analogs for labeling and colorimetric detection of DNA," Nucleic Acids Research, 15(11): 4513-4534 (1987).

Grantham, "Amino acid difference formula to help explain protein evolution," Science, 185: 862-864 (1974).

Guo et al, "Four-color DNA sequencing with 3'-O-modified nucleotide reversible terminators and chemically cleavable fluorescent dideoxynucleotides," Proc. Natl. Acad. Sci., 105(27): 9145-9150 (2008).

Guo et al, "An integrated system for DNA sequencing by synthesis using novel nucleotide analogues," Acc. Chem. Res., 43(4): 551-563 (2010).

Huang et al, "Multiple cleavage activities of endonuclease V from Thermotoga maritima: recognition and strand nicking mechanism," Biochemistry, 40: 8738-8748 (2001).

Hutter et al, "Labeled nucleoside triphosphates with reversibly terminating aminoalkoxyl groups," Nucleosides, Nucleotides & Nucleic Acids, 29(11): 879-895 (2010).

Integrated DNA Technologies brochure, "Strategies for Attaching Oligonucleotides to Solid Supports," v.6 (2014).

IPR2013-00128 re U.S. Pat. No. 7,057,026 Final Written Decision (dated Jul. 25, 2013).

IPR2013-00266 re U.S. Pat. No. 8,158,346 Final Written Decision (dated Oct. 28, 2014).

IPR2017-02172 re U.S. Pat. No. 7,566,537 Decision (dated Apr. 20, 2018).

Jensen et al, "Template-independent enzymatic oligonucleotide synthesis (TiEOS): Its history, prospects, and challenges," Biochemistry, 57: 1821-1832 (2018).

Ju et al, "Four-color DNA sequencing by synthesis using cleavable fluorescent nucleotide reversible terminators," Proc. Natl. Acad. Sci., 103(52): 19635-19640 (2006).

Knapp et al, "Fluoride-Cleavable, Fluorescently Labelled Reversible Terminators: Synthesis and Use in Primer Extension," Chem. Eur. J., 17: 2903-2915 (2011).

Kobayashi et al, "A microfluidic device for conducting gas-liquid-solid hydrogenation reactions," Science, 304: 1305-1308 (2004).

Kore et al, "Synthesis and activity of modified cytidine 5'-monophosphate probes for T4 RNA ligase 1," Nucleosides Nucleotides Nucleic Acids, 28(4): 292-302 (2009).

Lee et al, "Endonuclease V-mediated deoxyinosine excision repair in vitro," DNA Repair, 9: 1073-1079 (2010).

Li et al, "A photocleavable fluorescent nucleotide for DNA sequencing and analysis," Proc. Natl. Acad. Sci., 100(2): 414-419 (2003).

Lin et al, "Recent patents and advances in the next-generation sequencing technologies," Recent Patents in Biomedical Engineering, 2008(1): 60-67 (2008).

Mathews et al, "Photo-cleavable nucleotides for primer free enzyme mediated DNA synthesis," Organic & Biomolecular Chemistry, 14: 8278 (2016).

Mi et al, "Dissecting endonuclease and exonuclease activities in endonuclease V from Thermotoga maritime," Nucleic Acids Research, 39(2): 536-544 (2011).

Michelson et al, "Characterization of the homopolymer tailing reaction catalyzed by terminal deoxynucleotidyl transferase," J. Biol. Chem., 257(24): 14773-14782 (1982).

Morse et al, "Detection of inosine in messenger RNA by inosine-specific cleavage," Biochemistry, 36(28): (Jul. 15, 1997).

Motea et al, "Terminal deoxynucleotidyl transferase: The story of a misguided DNA polymerase," Biochim Biophys Acta, 1804(5): 1151-1166 (2010).

Olejnik et al, "Photocleavable biotin derivatives: A versatile approach for the isolation of biomolecules," Proc. Natl. Acad. Sci., 92: 7590-7594 (1995).

Palla et al, "DNA sequencing by synthesis using 3'-O-azidomethyl nucleotide reversible terminators and surface-enhanced Raman spectroscopic detection," RCS Adv. 4: 49342 (2014).

Petrie et al, "A novel biotinylated adenylate analogue derived from pyrazolo[3,4-d] pyrimidine for labeling DNA probes," Bioconjug. Chem., 2(6): 441-446 (1991).

Rasolonjatovo et al., "Development of a new sequencing method: 3'-ester cleavage catalyzed by Taq DNA polymerase," Nucleosides & Nucleotides, 18(4&5): 1021-1022 (1999).

Schmitz et al, "Solid-phase enzymatic synthesis of oligonucleotides," Organic Lett., 1(11): 1729-1731 (1999).

(56) References Cited

OTHER PUBLICATIONS

Schott et al, "Single-step elongation of oligodeoxynucleotides using terminal deoxynucleotidyl transferase," Eur. J. Biochem., 143: 613-620 (1984).
Taunton-Rigby, "Oligonucleotide synthesis. III. Enzymatically removable acyl protecting groups," J. Org. Chem., 38(5): 977-985 (1973).
Ud-Dean, "A theoretical model for template-free synthesis of long DNA sequence," Syst. Synth. Biol., 2: 67-73 (2008).
Uemura et al, "Regioselective deprotection of 3', 5'-O-acylated pyrimidine nucleosides by lipase and esterase," Tetrahedron Lett., 30(29): 3819-3820 (1989).
Vik et al, "Endonuclease V cleaves at inosine in RNA," Nature Communications, 4: article No. 2271 (2013).
Wu et al, "3'-O-modified nucleotides as reversible terminators for pyrosequencing," Proc. Natl. Acad. Sci., 104(42): 16462-16467 (2007).
Wu, Thesis, "Molecular engineering of novel nucleotide analogues for DNA sequencing by synthesis," Columbia University, 2008.
Yao et al, "Purification and characterization of a novel deoxyinosine-specific enzyme, deoxyinosine 3' endonuclease, from *Escherichia coli*," J. Biol. Chem., 269(23): 16260-16268 (1994).
Yao et al, "Interaction of deoxyinosine 3'-endonuclease from *Escherichia coli* with DNA containing deoxyinosine," J. Biol. Chem., 270 (48): 28609-28616 (1995).
Yao et al, "Further characterization of *Escherichia coli* Endonuclease V," J. Biol. Chem. 272(49): 30774-30779 (1997).
Zavgorodny et al, "1-Alkylthioalkylation of nucleoside hydroxyl functions and its synthetic applications: A new versatile method in nucleoside chemistry," Tetrahedron Lett., 32(51): 7593-7596 (1991).
Altschul et al., "Protein database searches using compositionally adjusted substitution matrices," FEBS Journal, 272: 5101-5109 (2005).
Altschul et al., "Gapped BLAST and PSI-BLAST: a new generation of protein database search programs," Nucleic Acids Research, 25(17): 3389-3402 (1997).
Meng et al., "Design and Synthesis of a Photocleavable Fluorescent Nucleotide 3'-O-Allyl-dGTP-PC-Bodipy-FL-510 as a Reversible Terminator for DNA Sequencing by Synthesis," J. Org. Chem., 71: 3248-3252 (2006).
Needleman et al., "A general method applicable to the search for similarities in the amino acid sequence of two proteins," J. Mol. Biol., 48: 443-453 (1970).
Smith et al., "Identification of common molecular subsequences," J. Mol. Biol., 147:195-197 (1981).

EFFICIENT PRODUCT CLEAVAGE IN TEMPLATE-FREE ENZYMATIC SYNTHESIS OF POLYNUCLEOTIDES

RELATED APPLICATIONS

The present application is a continuation application of U.S. application Ser. No. 16/981,595, entitled "EFFICIENT PRODUCT CLEAVAGE IN TEMPLATE-FREE ENZYMATIC SYNTHESIS OF POLYNUCLEOTIDES," filed on Sep. 16, 2020, which is a U.S. National Stage Entry of International Application No. PCT/EP2020/053417, entitled "EFFICIENT PRODUCT CLEAVAGE IN TEMPLATE-FREE ENZYMATIC SYNTHESIS OF POLYNUCLEOTIDES," filed on Feb. 11, 2020, which claims priority to European Application No. 19305174.5 filed on Feb. 12, 2019. All above-identified applications are hereby incorporated by reference in their entireties.

INCORPORATION OF SEQUENCE LISTING

A computer readable form of the Sequence Listing is filed with this application by electronic submission and is incorporated into this application by reference in its entirety. The Sequence Listing is contained in the file created on Nov. 28, 2022, having the file name P50390US01_SequenceListing.txt, and is 51,460 bytes in size (as measured in the MS-Windows® operating system).

BACKGROUND

Interest in enzymatic approaches to polynucleotide synthesis has recently increased both because of increased demand for synthetic polynucleotides in many areas, such as synthetic biology, CRISPR-Cas9 applications, high-throughput sequencing, and the like, and because of the limitations of chemical approaches to polynucleotide synthesis, Jensen et al, Biochemistry, 57: 1821-1832 (2018). Currently, most enzymatic approaches employ a template-free polymerase to repeatedly add 3'-O-blocked nucleoside triphosphates to a single stranded initiator or an elongated strand attached to a support followed by deblocking until a polynucleotide of the desired sequence is obtained. Among the challenges of devising a practical implementation of such enzymatic synthesis is to find a cost-effective and efficient way to cleave a desired polynucleotide product from the initiator sequence and the support.

In view of the above, enzymatic synthesis of polynucleotides would be advanced if methods were available for high efficiency cleavage of polynucleotide products from their single stranded initiators.

SUMMARY OF THE INVENTION

The present invention is directed to methods and kits for template-free enzymatic synthesis of polynucleotides that include or enable a step of efficiently cleaving the polynucleotide products from its initiator using an endonuclease V activity.

In one aspect, methods of the invention include a method of synthesizing polynucleotides of a predetermined sequence with the following steps: a) providing an initiator having a deoxyinosine penultimate to a 3'-terminal nucleotide having a free 3'-hydroxyl; b) repeating cycles of (i) contacting under elongation conditions the initiator or elongated fragments having free 3'-O-hydroxyls with a 3'-O-blocked nucleoside triphosphate and a template-independent DNA polymerase so that the initiator or elongated fragments are elongated by incorporation of a 3'-O-blocked nucleoside triphosphate to form 3'-O-blocked elongated fragments, and (ii) deblocking the elongated fragments to form elongated fragments having free 3'-hydroxyls, until the polynucleotide is formed; and c) treating the polynucleotide with an endonuclease V activity to cleave the polynucleotide from the initiator.

The present invention advantageously overcomes the above problems in the field of enzymatic polynucleotide synthesis by providing an initiator having a deoxyinosine at the penultimate position from its 3' end. This permits efficient cleavage of the single stranded initiator at its terminal nucleotide releasing a polynucleotide product with a 5'-monophosphate.

DETAILED DESCRIPTION OF THE INVENTION

Figure 1:
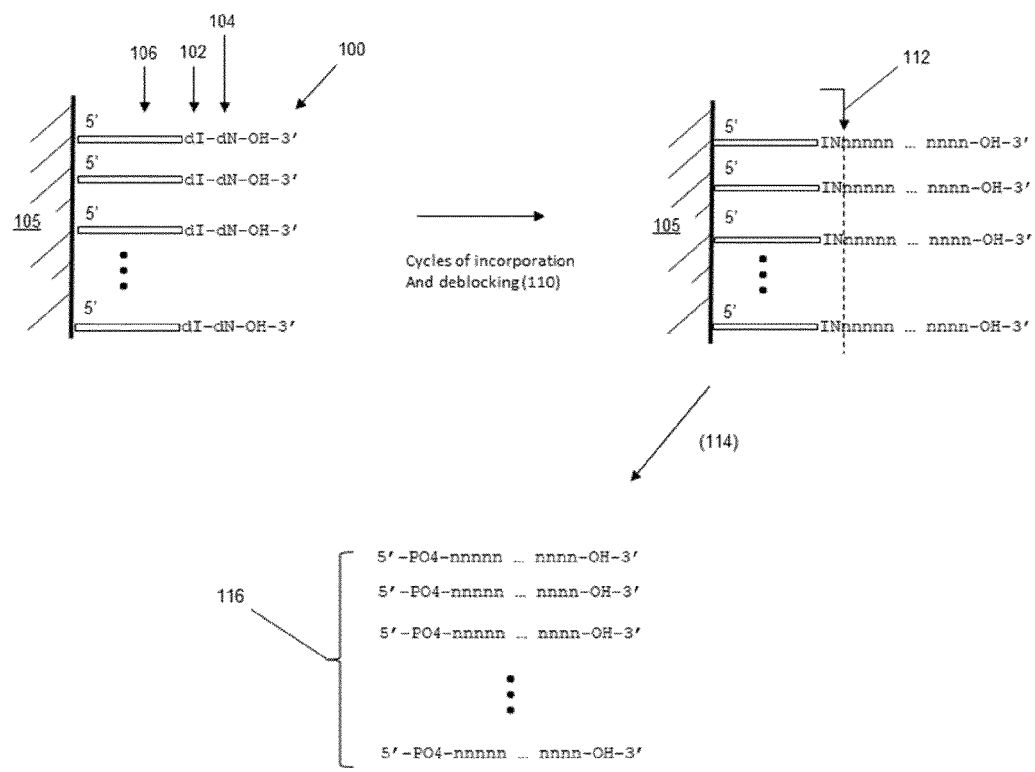
FIG. 1 illustrates an experimental set up for demonstrating the cleavage efficiency of the present invention.

The general principles of the invention are disclosed in more detail herein particularly by way of examples, such as those shown in the drawings and described in detail. It should be understood, however, that the intention is not to limit the invention to the particular embodiments described. The invention is amenable to various modifications and alternative forms, specifics of which are shown for several embodiments. The intention is to cover all modifications, equivalents, and alternatives falling within the principles and scope of the invention.

The practice of the present invention may employ, unless otherwise indicated, conventional techniques and descriptions of organic chemistry, molecular biology (including recombinant techniques), cell biology, and biochemistry, which are within the skill of the art. Such conventional techniques may include, but are not limited to, preparation and use of synthetic peptides, synthetic polynucleotides, monoclonal antibodies, nucleic acid cloning, amplification, sequencing and analysis, and related techniques. Protocols for such conventional techniques can be found in product literature from manufacturers and in standard laboratory manuals, such as Genome Analysis: A Laboratory Manual Series (Vols. I-IV); PCR Primer: A Laboratory Manual; and Molecular Cloning: A Laboratory Manual (all from Cold Spring Harbor Laboratory Press); Lutz and Bornscheuer, Editors, Protein Engineering Handbook (Wiley-VCH, 2009); Hermanson, Bioconjugate Techniques, Second Edition (Academic Press, 2008); and like references.

The present invention is based in part on a recognition and appreciation of the efficiency of using an endonuclesase V activity and a deoxyinosine penultimate to the 3' terminal nucleotide of an initiator to cleave a polynucleotide product from an initiator, as compared to other cleavable nucleotides, such as deoxyuridine. In one aspect, it is believed that synthesis initiation by a terminal deoxynucleotidyl transferase (TdT) on an initiator with a penultimate deoxyinosine is much more efficient than initiation on other cleavable nucleotide configurations.

FIG. 1 provides a diagram of a template-free enzymatic synthesis method employing initiators with a penultimate deoxyinosine. Shown in this depiction are initiators (100)

attached by their 5' ends to solid support (105). Each initiator (102) has a 3'-penultimate deoxyinosine (104) next to 3'-terminal nucleotide (106) that has a free 3' hydroxyl. After a predetermined number of cycles of enzymatic incorporation and de-blocking, a polynucleotide product is formed that is attached to solid support (105) by initiators (102). The polynucleotide product is cleaved from initiators (102) and support (105) by treating the attached product with an endonuclease V activity which recognizes the presence of the deoxyinosine and cleaves the strand on the 3' side (112) of terminal nucleotide (106) of the initiators. In some embodiments, the endonuclease V activity is provided by using a prokaryotic endonuclease V. In still other embodiments, the endonuclease V is an $E.\ coli$ endonuclease V. As used herein, the term "endonuclease V activity" means an enzyme activity that catalyzes the following cleavage reaction in a single stranded DNA: 5' . . . NNINNNN . . . -3'→ 5'- . . . NNIN +5'-$PO_4$-NNNN . . . -3' where N is any nucleotide and I is deoxyinosine. Cleavage (114) of polynucleotides (116) by an endonuclease V activity leaves a 5'-monophosphate on the polynucleotides, which optionally may be removed by a step of treating them with a 5'-phosphatase.

Enzymes with endonuclease V activity are available from commercial enzyme suppliers, for example, New England Biolabs (Beverly, Mass., USA), NzyTech (Lisbon, Portugal). Such enzymes may be used with the supplier's recommended cleavage buffers (e.g. 50 mM K—Ac, 20 mM Tris—Ac, 10 mM Mg—Ac, 1 mM DTT at pH 7.9). Typical cleavage conditions are as follows: 70 U of Endo V in 50 µl of Nzytech buffer at 37° C. for 500 pmol synthesis scale on resin. Typical cleavage times are from 5 to 60 minutes, or from 10 to 30 minutes. Optionally, endonuclease activity of the above enzymes may be heat inactivated by incubation at 65° C. or higher for 20 minutes. Optionally, the Nzytech endonuclease V comprises a His tag that allows convenient removal of the enzyme from reaction mixtures in preparation of final products.

Template-Free Enzymatic Synthesis

Template-free enzymatic synthesis of polynucleotides may be carried out by a variety of known protocols using template-free polymerases, such as terminal deoxynucleotidyl transferase (TdT), including variants thereof engineered to accommodate more efficiently 3'-O-blocked deoxynucleoside triphosphates (3'-O-blocked dNTPs), e.g. Ybert et al, International patent publication WO/2015/159023; Ybert et al, International patent publication WO/2017/216472; Hyman, U.S. Pat. No. 5,436,143; Hiatt et al, U.S. Pat. No. 5,763,594; Jensen et al, Biochemistry, 57: 1821-1832 (2018); Mathews et al, Organic & Biomolecular Chemistry, DOI: 0.1039/c6ob01371f (2016); Schmitz et al, Organic Lett., 1(11): 1729-1731 (1999).

In some embodiments, an ordered sequence of nucleotides is coupled to an initiator nucleic acid using a TdT in the presence of 3'-O-reversibly blocked dNTPs in each synthesis step. In some embodiments, the method of synthesizing an oligonucleotide comprises the steps of (a) providing an initiator having a free 3'-hydroxyl; (b) reacting under extension conditions the initiator or an extension intermediate having a free 3'-hydroxyl with a TdT in the presence of a 3'-O-blocked nucleoside triphosphate to produce a 3'-O-blocked extension intermediate; (c) deblocking the extension intermediate to produce an extension intermediate with a free 3'-hydroxyl; and (d) repeating steps (b) and (c) until the polynucleotide is synthesized. (Sometime "an extension intermediate" is also referred to as an "elongation fragment.") In some embodiments, an initiator is provided as an oligonucleotide attached to a solid support, e.g. by its 5' end. The above method may also include washing steps after the reaction, or extension, step, as well as after the de-blocking step. For example, the step of reacting may include a sub-step of removing unincorporated nucleoside triphosphates, e.g. by washing, after a predetermined incubation period, or reaction time. Such predetermined incubation periods or reaction times may be a few seconds, e.g. 30 sec, to several minutes, e.g. 30 min.

The above method may also include capping step(s) as well as washing steps after the reacting, or extending, step, as well as after the deblocking step. As mentioned above, in some embodiments, capping steps may be included in which non-extended free 3'-hydroxyls are reacted with compounds that prevents any further extensions of the capped strand. In some embodiments, such compound may be a dideoxynucleoside triphosphate. In other embodiments, non-extended strands with free 3'-hydroxyls may be degraded by treating them with a 3'-exonuclease activity, e.g. Exo I. For example, see Hyman, U.S. Pat. No. 5,436,143. Likewise, in some embodiments, strands that fail to be deblocked may be treated to either remove the strand or render it inert to further extensions.

In some embodiments that comprise serial synthesis of oligonucleotides, capping steps may be undesirable as capping may prevent the production of equal molar amounts of a plurality of oligonucleotides. Without capping, sequences will have a uniform distribution of deletion errors, but each of a plurality of oligonucleotides will be present in equal molar amounts. This would not be the case where non-extended fragments are capped.

In some embodiments, reaction conditions for an extension or elongation step may comprising the following: 2.0 µM purified TdT; 125-600 µM 3'-O-blocked dNTP (e.g. 3'-O-$NH_2$-blocked dNTP); about 10 to about 500 mM potassium cacodylate buffer (pH between 6.5 and 7.5) and from about 0.01 to about 10 mM of a divalent cation (e.g. $CoCl_2$ or $MnCl_2$), where the elongation reaction may be carried out in a 50 µL reaction volume, at a temperature within the range RT to 45° C., for 3 minutes. In embodiments, in which the 3'-O-blocked dNTPs are 3'-O—$NH_2$-blocked dNTPs, reaction conditions for a deblocking step may comprise the following: 700 mM $NaNO_2$; 1 M sodium acetate (adjusted with acetic acid to pH in the range of 4.8-6.5), where the deblocking reaction may be carried out in a 50 µL volume, at a temperature within the range of RT to 45° C. for 30 seconds to several minutes.

Depending on particular applications, the steps of deblocking and/or cleaving may include a variety of chemical or physical conditions, e.g. light, heat, pH, presence of specific reagents, such as enzymes, which are able to cleave a specified chemical bond. Guidance in selecting 3'-O-blocking groups and corresponding de-blocking conditions may be found in the following references, which are incorporated by reference: U.S. Pat. No. 5,808,045; U.S. Pat. No. 8,808,988; International patent publication WO91/06678; and references cited below. In some embodiments, the cleaving agent (also sometimes referred to as a de-blocking reagent or agent) is a chemical cleaving agent, such as, for example, dithiothreitol (DTT). In alternative embodiments, a cleaving agent may be an enzymatic cleaving agent, such as, for example, a phosphatase, which may cleave a 3'-phosphate blocking group. It will be understood by the person skilled in the art that the selection of deblocking agent depends on the type of 3'-nucleotide blocking group used, whether one or multiple blocking groups are being used, whether initiators are attached to living cells or organisms or to solid supports, and the like, that necessitate mild treatment. For example, a phosphine, such as tris(2-carboxyethyl)phosphine (TCEP) can be used to cleave a 3'-O-azidomethyl groups, palladium complexes can be used to cleave a 3'O-allyl groups, or sodium nitrite can be used to cleave a 3'O-amino group. In particular embodiments, the cleaving reaction involves TCEP, a palladium complex or sodium nitrite.

As noted above, in some embodiments it is desirable to employ two or more blocking groups that may be removed using orthogonal de-blocking conditions. The following exemplary pairs of blocking groups may be used in parallel synthesis embodiments, such as those described above. It is understood that other blocking group pairs, or groups containing more than two, may be available for use in these embodiments of the invention.

| | |
|---|---|
| 3'-O—NH2 | 3'-O-azidomethyl |
| 3'-O—NH2 | 3'-O-allyl |
| 3'-O—NH2 | 3'-O-phosphate |
| 3'-O-azidomethyl | 3'-O-allyl |
| 3'-O-azidomethyl | 3'-O-phosphate |
| 3'-O-allyl | 3'-O-phosphate |

Synthesizing oligonucleotides on living cells requires mild deblocking, or deprotection, conditions, that is, conditions that do not disrupt cellular membranes, denature proteins, interfere with key cellular functions, or the like. In some embodiments, deprotection conditions are within a range of physiological conditions compatible with cell survival. In such embodiments, enzymatic deprotection is desirable because it may be carried out under physiological conditions. In some embodiments specific enzymatically removable blocking groups are associated with specific enzymes for their removal. For example, ester- or acyl-based blocking groups may be removed with an esterase, such as acetylesterase, or like enzyme, and a phosphate blocking group may be removed with a 3' phosphatase, such as T4 polynucleotide kinase. By way of example, 3'-O-phosphates may be removed by treatment with as solution of 100 mM Tris—HCl (pH 6.5) 10 mM MgCl$_2$, 5 mM 2-mercaptoethanol, and one Unit T4 polynucleotide kinase. The reaction proceeds for one minute at a temperature of 37° C.

A "3'-phosphate-blocked" or "3'-phosphate-protected" nucleotide refers to nucleotides in which the hydroxyl group at the 3'-position is blocked by the presence of a phosphate containing moiety. Examples of 3'-phosphate-blocked nucleotides in accordance with the invention are nucleotidyl-3'-phosphate monoester/nucleotidyl-2',3'-cyclic phosphate, nucicotidyl-2'-phosphate monoester and nucleotidyl-2' or 3'-alkylphosphate diester, and nucleotidyl-2' or 3'-pyrophosphate. Thiophosphate or other analogs of such compounds can also be used, provided that the substitution does not prevent dephosphorylation resulting in a free 3'-OH by a phosphatase.

Further examples of synthesis and enzymatic deprotection of 3'-O-ester-protected dNTPs or 3'-O-phosphate-protected dNTPs are described in the following references: Canard et al, Proc. Natl. Acad. Sci., 92:10859-10863 (1995); Canard et al, Gene, 148: 1-6 (1994); Cameron et al, Biochemistry, 16(23): 5120-5126 (1977); Rasolonjatovo et al, Nucleosides & Nucleotides, 18(4&5): 1021-1022 (1999); Ferrero et al, Monatshefte fur Chemie, 131: 585-616 (2000); Taunton-Rigby et al, J. Org. Chem., 38(5): 977-985 (1973); Uemura et al, Tetrahedron Lett., 30(29): 3819-3820 (1989); Becker et al, J. Biol. Chem., 242(5): 936-950 (1967); Tsien, International patent publication WO1991/006678.

As used herein, an "initiator" (or equivalent terms, such as, "initiating fragment," "initiator nucleic acid," "initiator oligonucleotide," or the like) refers to a short oligonucleotide sequence with a free 3'-end, which can be further elongated by a template-free polymerase, such as TdT. In one embodiment, the initiating fragment is a DNA initiating fragment. In an alternative embodiment, the initiating fragment is an RNA initiating fragment. In one embodiment, the initiating fragment possesses between 3 and 100 nucleotides, in particular between 3 and 20 nucleotides. In one embodiment, the initiating fragment is single-stranded. In an alternative embodiment, the initiating fragment is double-stranded. In a particular embodiment, an initiator oligonucleotide synthesized with a 5'-primary amine may be covalently linked to magnetic beads using the manufacturer's protocol. Likewise, an initiator oligonucleotide synthesized with a 3'-primary amine may be covalently linked to magnetic beads using the manufacturer's protocol. A variety of other attachment chemistries amenable for use with embodiments of the invention are well-known in the art, e.g. Integrated DNA Technologies brochure, "Strategies for Attaching Oligonucleotides to Solid Supports," v.6 (2014); Hermanson, Bioconjugate Techniques, Second Edition (Academic Press, 2008); and like references.

Many of the 3'-O-blocked dNTPs employed in the invention may be purchased from commercial vendors or synthesized using published techniques, e.g. U.S. Pat. No. 7,057, 026; International patent publications WO2004/005667, WO91/06678; Canard et al, Gene (cited above); Metzker et al, Nucleic Acids Research, 22: 4259-4267 (1994); Meng et al, J. Org. Chem., 14: 3248-3252 (3006); U.S. patent publication 2005/037991. In some embodiments, the modified nucleotides comprise a modified nucleotide or nucleoside molecule comprising a purine or pyrimidine base and a ribose or deoxyribose sugar moiety having a removable 3'-OH blocking group covalently attached thereto, such that the 3' carbon atom has attached a group of the structure:

wherein —Z is any of —C(R')$_2$—O—R", —C(R')$_2$—N(R")$_2$, —C(R')$_2$—N(H)R", —C(R')$_2$—S—R" and —C(R')$_2$—F, wherein each R" is or is part of a removable protecting group; each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group; with the proviso that in some embodiments such substituents have up to 10 carbon atoms and/or up to 5 oxygen or nitrogen heteroatoms; or (R')$_2$ represents a group of formula =C(R''')$_2$ wherein each R''' may be the same or different and is selected from the group comprising hydrogen and halogen atoms and alkyl groups, with the proviso that in some embodiments the alkyl of each R''' has from 1 to 3 carbon atoms; and wherein the molecule may be reacted to yield an intermediate in which each R" is exchanged for H or, where Z is —(R')$_2$—F, the F is exchanged foSSr OH, SH or NH$_2$, preferably OH, which intermediate dissociates under aqueous conditions to afford a molecule with a free 3'-OH; with the proviso that where Z is —C(R')$_2$—S—R", both R' groups are not H. In certain embodiments, R' of the modified nucleotide or nucleoside is an alkyl or substituted alkyl, with the proviso that such alkyl or substituted alkyl has from 1 to 10 carbon atoms and from 0 to 4 oxygen or nitrogen heteroatoms. In certain embodiments, —Z of the modified nucleotide or nucleoside is of formula —C(R')$_2$—N3. In certain embodiments, Z is an azidomethyl group.

In some embodiments, Z is a cleavable organic moiety with or without heteroatoms having a molecular weight of 200 or less. In other embodiments, Z is a cleavable organic moiety with or without heteroatoms having a molecular weight of 100 or less. In other embodiments, Z is a cleavable organic moiety with or without heteroatoms having a molecular weight of 50 or less. In some embodiments, Z is an enzymatically cleavable organic moiety with or without heteroatoms having a molecular weight of 200 or less. In other embodiments, Z is an enzymatically cleavable organic moiety with or without heteroatoms having a molecular weight of 100 or less. In other embodiments, Z is an enzymatically cleavable organic moiety with or without heteroatoms having a molecular weight of 50 or less. In other embodiments, Z is an enzymatically cleavable ester group having a molecular weight of 200 or less. In other embodiments, Z is a phosphate group removable by a 3'-phosphatase. In some embodiments, one or more of the following 3'-phosphatases may be used with the manufacturer's recommended protocols: T4 polynucleotide kinase, calf intestinal alkaline phosphatase, recombinant shrimp alkaline phosphatase (e.g. available from New England Biolabs, Beverly, Mass.).

In a further particular embodiment, the 3'-blocked nucleotide triphosphate is blocked by either a 3'-O-azidomethyl, 3'-O—NH$_2$ or 3'-O-allyl group.

In still other embodiments, 3'-O-blocking groups of the invention include 3'-O-methyl, 3'-O-(2-nitrobenzyl), 3'-O-allyl, 3'-O-amine, 3-O-azidomethyl, 3'-O-tert-butoxy ethoxy, 3'-O-(2-cyanoethyl), and 3'-O-propargyl.

In some embodiments, 3'-O-protection groups are electrochemically labile groups. That is, deprotection or cleavage of the protection group is accomplished by changing the electrochemical conditions in the vicinity of the protection group which result in cleavage. Such changes in electrochemical conditions may be brought about by changing or applying a physical quantity, such as a voltage difference or light to activate auxiliary species which, in turn, cause changes in the electrochemical conditions at the site of the protection group, such as an increase or decrease in pH. In some embodiments, electrochemically labile groups include, for example, pH-sensitive protection groups that are cleaved whenever the pH is changed to a predetermined value. In other embodiments, electrochemically labile groups include protecting groups which are cleaved directly whenever reducing or oxidizing conditions are changed, for example, by increasing or decreasing a voltage difference at the site of the protection group.

In some embodiments, enzymatic synthesis methods employ TdT variants that display increased incorporation activity with respect to 3'-O-modified nucleoside triphosphates. For example, such TdT variants may be produced using techniques described in Champion et al, U.S. Pat. No. 10,435,676, which is incorporated herein by reference. In some embodiments, a TdT variant is employed having an amino acid sequence at least 60 percent identical to SEQ ID NO: 2 and a substitution at a first arginine at position 207 and a substitution at a second arginine at position 325, or functionally equivalent residues thereof. In some embodiments, a terminal deoxynucleotidyl transferase (TdT) variant is employed that has an amino acid sequence at least sixty percent identical to an amino acid sequence selected from SEQ ID NO: 2, 3, 4, 5, 6, 7, 8, 9, 10, 11, 12, 13, 14 or 15 with a substitution of arginine ("first arginine") at position 207 with respect to SEQ ID NOs 2, 3, 4, 6, 7, 9, 12 and 13, at position 206 with respect to SEQ ID NO 5, at position 208 with respect to SEQ ID NOs 8 and 10, at position 205 with respect to SEQ ID NO 11, at position 216 with respect to SEQ ID NO 14 and at position 210 with respect to SEQ ID NO 15; and a substitution of arginine ("second arginine") at position 325 with respect to SEQ ID NOs 2, 9 and 13, at position 324 with respect to SEQ ID NOs 3 and 4, at position 320 with respect to SEQ ID NO 320, at position 331 with respect to SEQ ID NOs 6 and 8, at position 323 with respect to SEQ ID NO 11, at position 328 with respect to SEQ ID NOs 12 and 15, and at position 338 with respect to SEQ ID NO 14; or functionally equivalent residues thereof wherein the TdT variant (i) is capable of synthesizing a nucleic acid fragment without a template and (ii) is capable of incorporating a 3'-O-modified nucleotide onto a free 3'-hydroxyl of a nucleic acid fragment. In some embodiments, the above percent identity value is at least 80 percent identity with the indicated SEQ ID NOs; in some embodiments, the above percent identity value is at least 90 percent identity with the indicated SEQ ID NOs; in some embodiments, the above percent identity value is at least 95 percent identity with the indicated SEQ ID NOs; in some embodiments, the above percent identity value is at least 97 percent identity; in some embodiments, the above percent identity value is at least 98 percent identity; in some embodiments, the above percent identity value is at least 99 percent identity. As used herein, the percent identity values used to compare a reference sequence to a variant sequence do not include the expressly specified amino acid positions containing substitutions of the variant sequence; that is, the percent identity relationship is between sequences of a reference protein and sequences of a variant protein outside of the expressly specified positions containing substitutions in the variant. Thus, for example, if the reference sequence and the variant sequence each comprised 100 amino acids and the variant sequence had mutations at positions 25 and 81, then the percent homology would be in regard to sequences 1-24, 26-80 and 82-100.

In regard to (ii), such 3'-O-modified nucleotide may comprise a 3'-O—NH2-nucleoside triphosphate, a 3'-O-azidomethyl-nucleoside triphosphate, a 3'-O-allyl-nucleoside triphosphate, a 3'O-(2-nitrobenzyl)-nucleoside triphosphate, or a 3'-O-propargyl-nucleoside triphosphate.

In some embodiments, TdT variants used in the invention have substitutions as shown in Table 1 or functionally equivalent residue positions in other TdTs.

TABLE 1

| SEQ ID NO | Substitutions | | | |
|---|---|---|---|---|
| 1 | M192R/Q | C302G/R | R336L/N | R454P/ N/A/V | E457N/ L/T/S/K |
| 2 | M63R/Q | C173G/R | R207L/N | R325P/ N/A/V | E328N/ L/T/S/K |
| 3 | M63R/Q | C173G/R | R207L/N | R324P/ N/A/V | E327N/ L/T/S/K |
| 4 | M63R/Q | C173G/R | R207L/N | R324P/ N/A/V | E327N/ L/T/S/K |
| 5 | — | C172G/R | R206L/N | R320P/ N/A/V | — |
| 6 | M63R/Q | C173G/R | R207L/N | R331P/ N/A/V | E334N/ L/T/S/K |
| 7 | M63R/Q | C173G/R | R207L/N | — | E328N/ L/T/S/K |
| 8 | — | C174G/R | R208L/N | R331P/ N/A/V | E334N/ L/T/S/K |
| 9 | M73R/Q | C173G/R | R207L/N | R325P/ N/A/V | E328N/ L/T/S/K |
| 10 | M64R/Q | C174G/R | R208L/N | — | E329N/ L/T/S/K |

TABLE 1-continued

| SEQ ID NO | Substitutions | | | | |
|---|---|---|---|---|---|
| 11 | M61R/Q | C171G/R | R205L/N | R323P/ N/A/V | E326N/ L/T/S/K |
| 12 | M63R/Q | C173G/R | R207L/N | R328P/ N/A/V | E331N/ L/T/S/K |
| 13 | — | C173G/R | R207L/N | R325P/ N/A/V | E328N/ L/T/S/K |
| 14 | M63R/Q | C182G/R | R216L/N | R338P/ N/A/V | E341N/ L/T/S/K |
| 15 | M66R/Q | C176G/R | R210L/N | R328P/ N/A/V | E331N/ L/T/S/K |

TdT variants of the invention as described above each comprise an amino acid sequence having a percent sequence identity with a specified SEQ ID NO, subject to the presence of indicated substitutions. In some embodiments, the number and type of sequence differences between a TdT variant of the invention described in this manner and the specified SEQ ID NO may be due to substitutions, deletion and/or insertions, and the amino acids substituted, deleted and/or inserted may comprise any amino acid. In some embodiments, such deletions, substitutions and/or insertions comprise only naturally occurring amino acids. In some embodiments, substitutions comprise only conservative, or synonymous, amino acid changes, as described in Grantham, Science, 185: 862-864 (1974). That is, a substitution of an amino acid can occur only among members of its set of synonymous amino acids. In some embodiments, sets of synonymous amino acids that may be employed are set forth in Table 2A.

TABLE 2A

Synonymous Sets of Amino Acids I

| Amino Acid | Synonymous Set |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Gly, Ala, Thr, Pro, Ser |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Cys, Ser, Thr |
| His | His, Glu, Lys, Gln, Thr, Arg |
| Gln | Gln, Glu, Lys, Asn, His, Thr, Arg |
| Asn | Asn, Gln, Asp, Ser |
| Lys | Lys, Glu, Gln, His, Arg |
| Asp | Asp, Glu, Asn |
| Glu | Glu, Asp, Lys, Asn, Gln, His, Arg |
| Met | Met, Phe, Ile, Val, Leu |
| Trp | Trp |

In some embodiments, sets of synonymous amino acids that may be employed are set forth in Table 2B.

TABLE 2B

Synonymous Sets of Amino Acids II

| Amino Acid | Synonymous Set |
|---|---|
| Ser | Ser |
| Arg | Arg, Lys, His |
| Leu | Ile, Phe, Met, Leu |
| Pro | Ala, Pro |
| Thr | Thr |
| Ala | Pro, Ala |
| Val | Met, Ile Val |
| Gly | Gly |
| Ile | Met, Phe, Val, Leu, Ile |
| Phe | Met, Tyr, Ile, Leu, Phe |
| Tyr | Trp, Met |
| Cys | Cys, Ser |
| His | His, Gln, Arg |
| Gln | Gln, Glu, His |
| Asn | Asn, Asp |
| Lys | Lys, Arg |
| Asp | Asp, Asn |
| Glu | Glu, Gln |
| Met | Met, Phe, Ile, Val, Leu |
| Trp | Trp |

Kits

The invention includes kits for carrying out methods of the invention. In some embodiments, a kit of the invention comprises an initiator attached to a support by a 5' end and having a deoxyinosine penultimate to a 3' end and free 3'-hydroxyl. In some embodiments, a kit of the invention further includes an endonuclease V capable of cleaving an initiator-polynucleotide conjugate 3' of a terminal nucleotide of the initiator. In some such kits, the endonuclease V has a capture moiety to permit removal from a reaction mixture. In some kits, such capture moiety is a His tag. In some embodiments, initiators of a kit have a 3'-terminal sequence of 5'-dI-dT-3'. In some embodiments, initiators of a kit have a 3'-terminal sequence of 5'-dI-dG-3'. In some embodiments, initiators of a kit have a 3'-terminal sequence of 5'-dI-dA-3'. In some embodiments, initiators of a kit have a 3'-terminal sequence of 5'-dI-dT-3', 5'-dI-dG-3', or 5'-dI-dA-3'. In some embodiments, such support is a solid support. Such solid support may comprise beads, such as magnetic bead, a planar solid, such as a glass slide, or a membrane, or the like. In some embodiments, a kit of the invention may further include a template-free polymerase and 3'-O-blocked nucleoside triphosphates of one or more of deoxyadenosine, deoxyguanosine, thymidine, deoxyuridine and deoxycytidine. In some kits, such template-free polymerase may be a TdT. In some embodiments, such TdT may be a TdT variant described herein. In some embodiments, a kit of the invention may further include a de-blocking agent which is capable of removing 3' blocking groups from incorporated 3'-O-blocked nucleotides.

EXAMPLE

In this example, the efficiency of using deoxyinosine/endo V cleavage is compared to deoxyuridine/USER cleavage and the effects on cleavage of nucleotides adjacent to dI are assessed. 5'-amino-poly(dT) oligonucleotides containing dI were coupled to carboxyl groups of magnetic beads using EDC in a conventional reaction. In all experiments, initiators comprised either (1) a 5'-10mer polyT segment followed by a deoxyinosine and 3' terminal dT, or (2) a 5'-10mer polyT segment followed by a terminal deoxyuridine. In some experiments, initiators were extended by a 20mer polyT segment followed by a final dA labeled with a Cy5 dye, all using a TdT enzyme and 3'-O—NH$_2$-blocked nucleoside triphosphates (except for the labeled terminal dA). In other experiments, the initiators were extended by the indicated dinucleotide sequences followed by a 18mer poly(dT) and a final dA labeled with a Cy5 dye, all using a TdT enzyme and 3'-O—NH$_2$-blocked nucleoside triphosphates (except for the labeled terminal dA). After cleavage as indicated (USER or Endo V), the cleaved labeled polynucleotides were analyzed by polyacrylamide gel electrophoresis.

Figure 2:
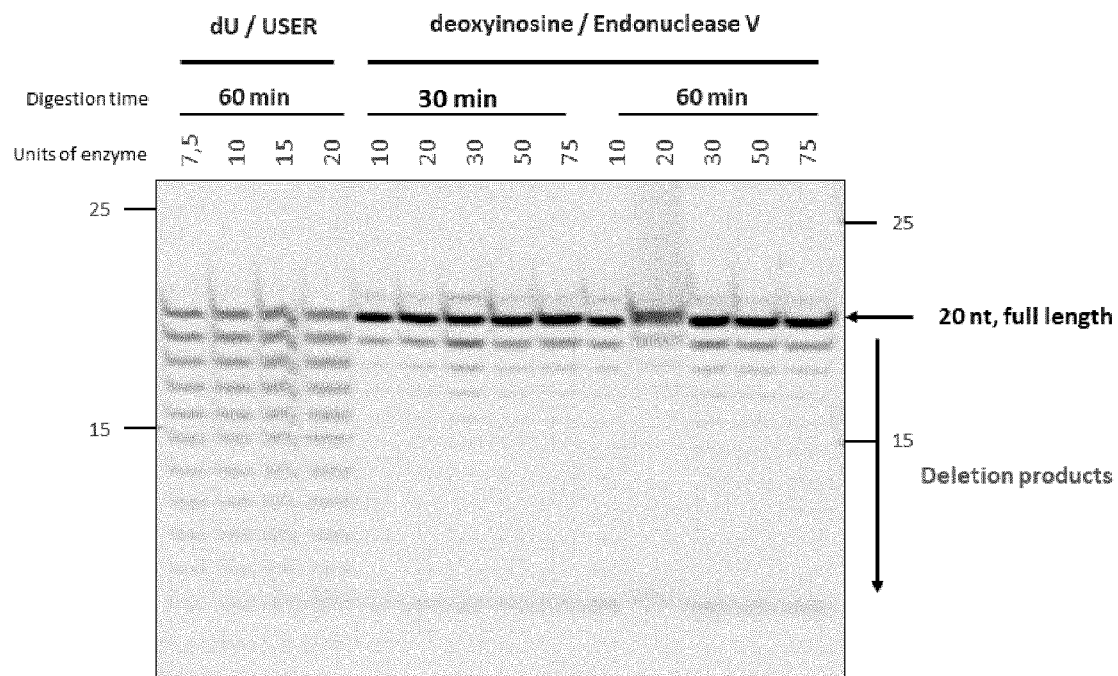
FIG. 2 shows data comparing efficiencies of USER/deoxyuridine cleavage and Endo V/inosine cleavage.

FIG. 2 shows electrophoresis data comparing synthesis products of initiators having terminal deoxyuridines with synthesis products of initiators having penultimate deoxyinosines. The bands in the four ladders on the left of the gel corresponding to deoxyuridine initiators show failure sequences that are significantly more intense than the corresponding bands from deoxyinosine initiators in the rightmost 10 ladders indicating that initiators with penultimate deoxyinosines result in more efficient synthesis than initiators with terminal deoxyuridines.

Definitions

Unless otherwise specifically defined herein, terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999).

"Functionally equivalent" in reference to amino acid positions in two or more different TdTs means (i) the amino acids at the respective positions play the same functional role in an activity of the TdTs, and (ii) the amino acids occur at homologous amino acid positions in the amino acid sequences of the respective TdTs. It is possible to identify positionally equivalent or homologous amino acid residues in the amino acid sequences of two or more different TdTs on the basis of sequence alignment and/or molecular modelling. In some embodiments, functionally equivalent amino acid positions belong to sequence motifs that are conserved among the amino acid sequences of TdTs of evolutionarily related species, e.g. genus, families, or the like. Examples of such conserved sequence motifs are described in Motea et al, Biochim. Biophys. Acta. 1804(5): 1151-1166 (2010); Delarue et al, EMBO J., 21: 427-439 (2002); and like references.

"Kit" refers to any delivery system for delivering materials or reagents for carrying out a method of the invention. In the context of reaction assays, such delivery systems include systems and/or compounds (such as dilutants, surfactants, carriers, or the like) that allow for the storage, transport, or delivery of reaction reagents (e.g., fluorescent labels, such as mutually quenching fluorescent labels, fluorescent label linking agents, enzymes, quenching agents, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second or more containers contain mutually quenching fluorescent labels and/or quenching agents.

"Mutant" or "variant," which are used interchangeably, refer to polypeptides derived from a natural or reference TdT polypeptide described herein, and comprising a modification or an alteration, i.e., a substitution, insertion, and/or deletion, at one or more positions. Variants may be obtained by various techniques well known in the art. In particular, examples of techniques for altering the DNA sequence encoding the wild-type protein, include, but are not limited to, site-directed mutagenesis, random mutagenesis, sequence shuffling and synthetic oligonucleotide construction. Mutagenesis activities consist in deleting, inserting or substituting one or several amino-acids in the sequence of a protein or in the case of the invention of a polymerase.

"Polynucleotide" or "oligonucleotide" are used interchangeably and each mean a linear polymer of nucleotide monomers or analogs thereof. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references. Likewise, the oligonucleotide and polynucleotide may refer to either a single stranded form or a double stranded form (i.e. duplexes of an oligonucleotide or polynucleotide and its respective complement). It will be clear to one of ordinary skill which form or whether both forms are intended from the context of the terms usage.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual, 2nd Edition (Cold Spring Harbor Press, New York, 2003).

"Sequence identity" refers to the number (or fraction, usually expressed as a percentage) of matches (e.g., identical amino acid residues) between two sequences, such as two polypeptide sequences or two polynucleotide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithm (e.g. Needleman and Wunsch algorithm; Needleman and Wunsch, 1970) which aligns the sequences optimally over the entire length, while sequences of substantially different lengths are preferably aligned using a local alignment algorithm (e.g. Smith and Waterman algorithm (Smith and Waterman, 1981) or Altschul algorithm (Altschul et al., 1997; Altschul et al., 2005)). Alignment for purposes of determining percent amino acid sequence identity can be achieved in various ways that are within the skill in the art, for instance, using publicly available computer software available on internet web sites. Those skilled in the art can determine appropriate parameters for measuring alignment, including any algorithm needed to achieve maximal alignment over the full length of the sequences being compared. For purposes herein, % amino acid sequence identity values refer to values generated using the pair wise sequence alignment program EMBOSS Needle, that creates an optimal global alignment of two sequences using the Needleman-Wunsch algorithm, wherein all search parameters are set to default values, i.e. Scoring matrix=BLOSUM62, Gap open=10, Gap extend=0.5, End gap penalty=false, End gap open=10 and End gap extend=0.5.

A "substitution" means that an amino acid residue is replaced by another amino acid residue. Preferably, the term "substitution" refers to the replacement of an amino acid residue by another selected from the naturally-occurring standard 20 amino acid residues, rare naturally occurring amino acid residues (e.g. hydroxyproline, hydroxylysine, allohydroxylysine, 6-N-methylysine, N-ethylglycine, N-methylglycine, N-ethylasparagine, allo-isoleucine, N-methylisoleucine, N-methylvaline, pyroglutamine, aminobutyric acid, ornithine, norleucine, norvaline), and non-naturally occurring amino acid residue, often made synthetically, (e.g. cyclohexyl-alanine). Preferably, the term "substitution" refers to the replacement of an amino acid residue by another selected from the naturally-occurring standard 20 amino acid residues. The sign "+" indicates a combination of substitutions. The amino acids are herein represented by their one-letter or three-letters code according to the following nomenclature: A: alanine (Ala); C: cysteine (Cys); D: aspartic acid (Asp); E: glutamic acid (Glu); F: phenylalanine (Phe); G: glycine (Gly); H: histidine (His); I: isoleucine (Ile); K: lysine (Lys); L: leucine (Leu); M: methionine (Met); N: asparagine (Asn); P: proline (Pro); Q: glutamine (Gln); R: arginine (Arg); S: serine (Ser); T: threonine (Thr); V: valine (Val); W: tryptophan (Trp) and Y: tyrosine (Tyr). In the present document, the following terminology is used to designate a substitution: L238A denotes that amino acid residue (Leucine, L) at position 238 of the parent sequence is changed to an Alanine (A). A132V/I/M denotes that amino acid residue (Alanine, A) at position 132 of the parent sequence is substituted by one of the following amino acids: Valine (V), Isoleucine (I), or Methionine (M). The substitution can be a conservative or non-conservative substitution. Examples of conservative substitutions are within the groups of basic amino acids (arginine, lysine and histidine), acidic amino acids (glutamic acid and aspartic acid), polar amino acids (glutamine, asparagine and threonine), hydrophobic amino acids (methionine, leucine, isoleucine, cysteine and valine), aromatic amino acids (phenylalanine, tryptophan and tyrosine), and small amino acids (glycine, alanine and serine).

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

The invention claimed is:

1. A method of synthesizing a polynucleotide having a predetermined sequence, the method comprising the steps of:
   a) providing an initiator having a 3'-penultimate deoxyinosine and a 3'-terminal nucleotide having a free 3'-hydroxyl;
   b) repeating cycles of (i) contacting under elongation conditions the initiator or elongated fragments having free 3'-O-hydroxyls with a 3'-O-blocked nucleoside triphosphate and a template-independent DNA polymerase so that the initiator or elongated fragments are elongated by incorporation of the 3'-O-blocked nucleoside triphosphate to form 3'-O-blocked elongated fragments, and (ii) deblocking the elongated fragments to form elongated fragments having free 3'-hydroxyls, until the polynucleotide is formed, wherein said template-independent DNA polymerase is a terminal deoxynucleotidyl transferase; and
   c) treating the polynucleotide with an endonuclease V activity to cleave the polynucleotide from the initiator, wherein said endonuclease V activity is provided by a prokaryotic endonuclease V.

2. The method of claim 1, wherein said prokaryotic endonuclease V is an E. coli endonuclease V.

3. The method of claim 1, further comprising a step of removing said prokaryotic endonuclease V from said cleaved polynucleotide.

4. The method of claim 1, wherein said initiator is attached to a support by a 5' end.

5. The method of claim 4, wherein said support is a solid support.

6. The method of claim 1, wherein said initiator has a 3'-terminal sequence of 5'-dI-dT-3'.

7. The method of claim 1, wherein said polynucleotide cleaved from said initiator has a 5'-monophosphate.

8. A kit for enzymatically synthesizing a polynucleotide comprising an initiator attached to a support by a 5' end and having a 3'-penultimate deoxyinosine; a 3'-terminal nucleotide having a free 3'-hydroxyl; an endonuclease V capable of cleaving an initiator-polynucleotide conjugate 3' of a terminal nucleotide of the initiator; the template-free polymerase terminal deoxynucleotidyl transferase; and a 3'-O-blocked nucleoside triphosphate for one or more of deoxyadenosine, deoxyguanosine, thymidine, deoxyuridine and deoxycytidine.

9. The kit of claim 8, further comprising said initiator with a 3'-terminal sequence of 5'-dI-dT-3'.

10. The kit of claim 8, wherein said support is a solid support.

11. The kit of claim 8, further comprising a de-blocking agent.

12. The kit of claim 8 wherein said 3'-O-blocked nucleoside triphosphate is 3'-O-NH$_2$-nucleoside triphosphate.

13. The method of claim 2, further comprising a step of removing said prokaryotic endonuclease V from said cleaved polynucleotide.

14. The method of claim 2, wherein said initiator is attached to a support by a 5' end.

15. The method of claim 14, wherein said support is a solid support.

* * * * *

UNITED STATES PATENT AND TRADEMARK OFFICE
CERTIFICATE OF CORRECTION

| | |
|---|---|
| PATENT NO. | : 11,905,541 B2 |
| APPLICATION NO. | : 17/837660 |
| DATED | : February 20, 2024 |
| INVENTOR(S) | : Sandrine Creton |

It is certified that error appears in the above-identified patent and that said Letters Patent is hereby corrected as shown below:

In the Claims

Claim 8 in Column 46, Lines 42-51 should read as follows:
8. A kit for enzymatically synthesizing a polynucleotide comprising an initiator attached to a support by a 5′ end and having a 3'-penultimate deoxyinosine and a 3'-terminal nucleotide having a free 3'-hydroxyl; an endonuclease V capable of cleaving an initiator-polynucleotide conjugate 3' of a terminal nucleotide of the initiator; a template-free polymerase terminal deoxynucleotidyl transferase; and a 3'-O-blocked nucleoside triphosphate for one or more of deoxyadenosine, deoxyguanosine, thymidine, deoxyuridine and deoxycytidine.

Signed and Sealed this
Fifth Day of November, 2024

Katherine Kelly Vidal
*Director of the United States Patent and Trademark Office*

SEQUENCE LISTING

<160> NUMBER OF SEQ ID NOS: 15

<210> SEQ ID NO 1
<211> LENGTH: 510
<212> TYPE: PRT
<213> ORGANISM: ARTIFICIAL SEQUENCE
<220> FEATURE:
<223> OTHER INFORMATION: TdT

<400> SEQUENCE: 1

Met Asp Pro Leu Gln Ala Val His Leu Gly Pro Arg Lys Lys Arg Pro
1               5                   10                  15

```
Arg Gln Leu Gly Thr Pro Val Ala Ser Thr Pro Tyr Asp Ile Arg Phe
            20                  25                  30

Arg Asp Leu Val Leu Phe Ile Leu Glu Lys Met Gly Thr Thr Arg
        35                  40                  45

Arg Ala Phe Leu Met Glu Leu Ala Arg Arg Lys Gly Phe Arg Val Glu
50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Leu Gln Asn Ile Lys Ala Ser
                85                  90                  95

Ser Glu Leu Glu Leu Leu Asp Ile Ser Trp Leu Ile Glu Cys Met Gly
            100                 105                 110

Ala Gly Lys Pro Val Glu Met Met Gly Arg His Gln Leu Val Val Asn
        115                 120                 125

Arg Asn Ser Ser Pro Ser Pro Val Pro Gly Ser Gln Asn Val Pro Ala
130                 135                 140

Pro Ala Val Lys Lys Ile Ser Gln Tyr Ala Cys Gln Arg Arg Thr Thr
145                 150                 155                 160

Leu Asn Asn Tyr Asn Gln Leu Phe Thr Asp Ala Leu Asp Ile Leu Ala
                165                 170                 175

Glu Asn Asp Glu Leu Arg Glu Asn Gly Ser Cys Leu Ala Phe Met
            180                 185                 190

Arg Ala Ser Ser Val Leu Lys Ser Leu Pro Phe Pro Ile Thr Ser Met
        195                 200                 205

Lys Asp Thr Glu Gly Ile Pro Cys Leu Gly Asp Lys Val Lys Ser Ile
210                 215                 220

Ile Glu Gly Ile Ile Glu Asp Gly Glu Ser Ser Glu Ala Lys Ala Val
225                 230                 235                 240

Leu Asn Asp Glu Arg Tyr Lys Ser Phe Lys Leu Phe Thr Ser Val Phe
                245                 250                 255

Gly Val Gly Leu Lys Thr Ala Glu Lys Trp Phe Arg Met Gly Phe Arg
            260                 265                 270

Thr Leu Ser Lys Ile Gln Ser Asp Lys Ser Leu Arg Phe Thr Gln Met
        275                 280                 285

Gln Lys Ala Gly Phe Leu Tyr Tyr Glu Asp Leu Val Ser Cys Val Asn
290                 295                 300

Arg Pro Glu Ala Glu Ala Val Ser Met Leu Val Lys Glu Ala Val Val
305                 310                 315                 320

Thr Phe Leu Pro Asp Ala Leu Val Thr Met Thr Gly Gly Phe Arg Arg
                325                 330                 335

Gly Lys Met Thr Gly His Asp Val Asp Phe Leu Ile Thr Ser Pro Glu
            340                 345                 350

Ala Thr Glu Asp Glu Glu Gln Gln Leu Leu His Lys Val Thr Asp Phe
        355                 360                 365

Trp Lys Gln Gln Gly Leu Leu Leu Tyr Cys Asp Ile Leu Glu Ser Thr
370                 375                 380

Phe Glu Lys Phe Lys Gln Pro Ser Arg Lys Val Asp Ala Leu Asp His
385                 390                 395                 400

Phe Gln Lys Cys Phe Leu Ile Leu Lys Leu Asp His Gly Arg Val His
                405                 410                 415

Ser Glu Lys Ser Gly Gln Gln Glu Gly Lys Gly Trp Lys Ala Ile Arg
            420                 425                 430
```

```
Val Asp Leu Val Met Cys Pro Tyr Asp Arg Arg Ala Phe Ala Leu Leu
            435                 440                 445

Gly Trp Thr Gly Ser Arg Gln Phe Glu Arg Asp Leu Arg Arg Tyr Ala
450                 455                 460

Thr His Glu Arg Lys Met Met Leu Asp Asn His Ala Leu Tyr Asp Arg
465                 470                 475                 480

Thr Lys Arg Val Phe Leu Glu Ala Glu Ser Glu Glu Ile Phe Ala
                485                 490                 495

His Leu Gly Leu Asp Tyr Ile Glu Pro Trp Glu Arg Asn Ala
            500                 505                 510

<210> SEQ ID NO 2
<211> LENGTH: 381
<212> TYPE: PRT
<213> ORGANISM: ARTIFICIAL SEQUENCE
<220> FEATURE:
<223> OTHER INFORMATION: truncated mouse TdT

<400> SEQUENCE: 2

Asn Ser Ser Pro Ser Pro Val Pro Gly Ser Gln Asn Val Pro Ala Pro
1               5                   10                  15

Ala Val Lys Lys Ile Ser Gln Tyr Ala Cys Gln Arg Arg Thr Thr Leu
            20                  25                  30

Asn Asn Tyr Asn Gln Leu Phe Thr Asp Ala Leu Asp Ile Leu Ala Glu
        35                  40                  45

Asn Asp Glu Leu Arg Glu Asn Glu Gly Ser Cys Leu Ala Phe Met Arg
    50                  55                  60

Ala Ser Ser Val Leu Lys Ser Leu Pro Phe Pro Ile Thr Ser Met Lys
65                  70                  75                  80

Asp Thr Glu Gly Ile Pro Cys Leu Gly Asp Lys Val Lys Ser Ile Ile
                85                  90                  95

Glu Gly Ile Ile Glu Asp Gly Glu Ser Ser Glu Ala Lys Ala Val Leu
            100                 105                 110

Asn Asp Glu Arg Tyr Lys Ser Phe Lys Leu Phe Thr Ser Val Phe Gly
        115                 120                 125

Val Gly Leu Lys Thr Ala Glu Lys Trp Phe Arg Met Gly Phe Arg Thr
    130                 135                 140

Leu Ser Lys Ile Gln Ser Asp Lys Ser Leu Arg Phe Thr Gln Met Gln
145                 150                 155                 160

Lys Ala Gly Phe Leu Tyr Tyr Glu Asp Leu Val Ser Cys Val Asn Arg
                165                 170                 175

Pro Glu Ala Glu Ala Val Ser Met Leu Val Lys Glu Ala Val Val Thr
            180                 185                 190

Phe Leu Pro Asp Ala Leu Val Thr Met Thr Gly Gly Phe Arg Arg Gly
        195                 200                 205

Lys Met Thr Gly His Asp Val Asp Phe Leu Ile Thr Ser Pro Glu Ala
    210                 215                 220

Thr Glu Asp Glu Glu Gln Gln Leu Leu His Lys Val Thr Asp Phe Trp
225                 230                 235                 240

Lys Gln Gln Gly Leu Leu Leu Tyr Cys Asp Ile Leu Glu Ser Thr Phe
                245                 250                 255

Glu Lys Phe Lys Gln Pro Ser Arg Lys Val Asp Ala Leu Asp His Phe
            260                 265                 270

Gln Lys Cys Phe Leu Ile Leu Lys Leu Asp His Gly Arg Val His Ser
        275                 280                 285
```

```
Glu Lys Ser Gly Gln Gln Glu Gly Lys Gly Trp Lys Ala Ile Arg Val
    290                 295                 300

Asp Leu Val Met Cys Pro Tyr Asp Arg Arg Ala Phe Ala Leu Leu Gly
305                 310                 315                 320

Trp Thr Gly Ser Arg Gln Phe Glu Arg Asp Leu Arg Arg Tyr Ala Thr
                325                 330                 335

His Glu Arg Lys Met Met Leu Asp Asn His Ala Leu Tyr Asp Arg Thr
                340                 345                 350

Lys Arg Val Phe Leu Glu Ala Glu Ser Glu Glu Ile Phe Ala His
                355                 360                 365

Leu Gly Leu Asp Tyr Ile Glu Pro Trp Glu Arg Asn Ala
370                 375                 380
```

<210> SEQ ID NO 3
<211> LENGTH: 380
<212> TYPE: PRT
<213> ORGANISM: BOS TAURUS

<400> SEQUENCE: 3

```
Asp Tyr Ser Ala Thr Pro Asn Pro Gly Phe Gln Lys Thr Pro Pro Leu
1               5                   10                  15

Ala Val Lys Lys Ile Ser Gln Tyr Ala Cys Gln Arg Lys Thr Thr Leu
                20                  25                  30

Asn Asn Tyr Asn His Ile Phe Thr Asp Ala Phe Glu Ile Leu Ala Glu
                35                  40                  45

Asn Ser Glu Phe Lys Glu Asn Glu Val Ser Tyr Val Thr Phe Met Arg
    50                  55                  60

Ala Ala Ser Val Leu Lys Ser Leu Pro Phe Thr Ile Ile Ser Met Lys
65                  70                  75                  80

Asp Thr Glu Gly Ile Pro Cys Leu Gly Asp Lys Val Lys Cys Ile Ile
                85                  90                  95

Glu Glu Ile Ile Glu Asp Gly Glu Ser Ser Glu Val Lys Ala Val Leu
                100                 105                 110

Asn Asp Glu Arg Tyr Gln Ser Phe Lys Leu Phe Thr Ser Val Phe Gly
                115                 120                 125

Val Gly Leu Lys Thr Ser Glu Lys Trp Phe Arg Met Gly Phe Arg Ser
    130                 135                 140

Leu Ser Lys Ile Met Ser Asp Lys Thr Leu Lys Phe Thr Lys Met Gln
145                 150                 155                 160

Lys Ala Gly Phe Leu Tyr Tyr Glu Asp Leu Val Ser Cys Val Thr Arg
                165                 170                 175

Ala Glu Ala Glu Ala Val Gly Val Leu Val Lys Glu Ala Val Trp Ala
                180                 185                 190

Phe Leu Pro Asp Ala Phe Val Thr Met Thr Gly Gly Phe Arg Arg Gly
                195                 200                 205

Lys Lys Ile Gly His Asp Val Asp Phe Leu Ile Thr Ser Pro Gly Ser
    210                 215                 220

Ala Glu Asp Glu Glu Gln Leu Leu Pro Lys Val Ile Asn Leu Trp Glu
225                 230                 235                 240

Lys Lys Gly Leu Leu Leu Tyr Tyr Asp Leu Val Glu Ser Thr Phe Glu
                245                 250                 255

Lys Phe Lys Leu Pro Ser Arg Gln Val Asp Thr Leu Asp His Phe Gln
                260                 265                 270

Lys Cys Phe Leu Ile Leu Lys Leu His His Gln Arg Val Asp Ser Ser
                275                 280                 285
```

```
Lys Ser Asn Gln Gln Glu Gly Lys Thr Trp Lys Ala Ile Arg Val Asp
    290                 295                 300

Leu Val Met Cys Pro Tyr Glu Asn Arg Ala Phe Ala Leu Leu Gly Trp
305                 310                 315                 320

Thr Gly Ser Arg Gln Phe Glu Arg Asp Ile Arg Arg Tyr Ala Thr His
                325                 330                 335

Glu Arg Lys Met Met Leu Asp Asn His Ala Leu Tyr Asp Lys Thr Lys
                340                 345                 350

Arg Val Phe Leu Lys Ala Glu Ser Glu Glu Ile Phe Ala His Leu
            355                 360                 365

Gly Leu Asp Tyr Ile Glu Pro Trp Glu Arg Asn Ala
    370                 375                 380

<210> SEQ ID NO 4
<211> LENGTH: 380
<212> TYPE: PRT
<213> ORGANISM: HOMO SAPIENS

<400> SEQUENCE: 4

Asp Tyr Ser Asp Ser Thr Asn Pro Gly Pro Pro Lys Thr Pro Pro Ile
1               5                   10                  15

Ala Val Gln Lys Ile Ser Gln Tyr Ala Cys Gln Arg Arg Thr Thr Leu
                20                  25                  30

Asn Asn Cys Asn Gln Ile Phe Thr Asp Ala Phe Asp Ile Leu Ala Glu
            35                  40                  45

Asn Cys Glu Phe Arg Glu Asn Glu Asp Ser Cys Val Thr Phe Met Arg
50                  55                  60

Ala Ala Ser Val Leu Lys Ser Leu Pro Phe Thr Ile Ile Ser Met Lys
65                  70                  75                  80

Asp Thr Glu Gly Ile Pro Cys Leu Gly Ser Lys Val Lys Gly Ile Ile
                85                  90                  95

Glu Glu Ile Ile Glu Asp Gly Glu Ser Ser Val Lys Ala Val Leu
            100                 105                 110

Asn Asp Glu Arg Tyr Gln Ser Phe Lys Leu Phe Thr Ser Val Phe Gly
            115                 120                 125

Val Gly Leu Lys Thr Ser Glu Lys Trp Phe Arg Met Gly Phe Arg Thr
130                 135                 140

Leu Ser Lys Val Arg Ser Asp Lys Ser Leu Lys Phe Thr Arg Met Gln
145                 150                 155                 160

Lys Ala Gly Phe Leu Tyr Tyr Glu Asp Leu Val Ser Cys Val Thr Arg
                165                 170                 175

Ala Glu Ala Glu Ala Val Ser Val Leu Val Lys Glu Ala Val Trp Ala
            180                 185                 190

Phe Leu Pro Asp Ala Phe Val Thr Met Thr Gly Gly Phe Arg Arg Gly
        195                 200                 205

Lys Lys Met Gly His Asp Val Asp Phe Leu Ile Thr Ser Pro Gly Ser
    210                 215                 220

Thr Glu Asp Glu Glu Gln Leu Leu Gln Lys Val Met Asn Leu Trp Glu
225                 230                 235                 240

Lys Lys Gly Leu Leu Leu Tyr Tyr Asp Leu Val Glu Ser Thr Phe Glu
                245                 250                 255

Lys Leu Arg Leu Pro Ser Arg Lys Val Asp Ala Leu Asp His Phe Gln
            260                 265                 270

Lys Cys Phe Leu Ile Phe Lys Leu Pro Arg Gln Arg Val Asp Ser Asp
```

```
                    275                 280                 285
Gln Ser Ser Trp Gln Glu Gly Lys Thr Trp Lys Ala Ile Arg Val Asp
    290                 295                 300

Leu Val Leu Cys Pro Tyr Glu Arg Arg Ala Phe Ala Leu Leu Gly Trp
305                 310                 315                 320

Thr Gly Ser Arg Gln Phe Glu Arg Asp Leu Arg Arg Tyr Ala Thr His
                325                 330                 335

Glu Arg Lys Met Ile Leu Asp Asn His Ala Leu Tyr Asp Lys Thr Lys
                340                 345                 350

Arg Ile Phe Leu Lys Ala Glu Ser Glu Glu Ile Phe Ala His Leu
                355                 360                 365

Gly Leu Asp Tyr Ile Glu Pro Trp Glu Arg Asn Ala
                370                 375                 380
```

<210> SEQ ID NO 5
<211> LENGTH: 376
<212> TYPE: PRT
<213> ORGANISM: GALLUS GALLUS

<400> SEQUENCE: 5

```
Gln Tyr Pro Thr Leu Lys Thr Pro Glu Ser Glu Val Ser Ser Phe Thr
1               5                   10                  15

Ala Ser Lys Val Ser Gln Tyr Ser Cys Gln Arg Lys Thr Thr Leu Asn
            20                  25                  30

Asn Cys Asn Lys Lys Phe Thr Asp Ala Phe Glu Ile Met Ala Glu Asn
        35                  40                  45

Tyr Glu Phe Lys Glu Asn Glu Ile Phe Cys Leu Glu Phe Leu Arg Ala
    50                  55                  60

Ala Ser Val Leu Lys Ser Leu Pro Phe Pro Val Thr Arg Met Lys Asp
65                  70                  75                  80

Ile Gln Gly Leu Pro Cys Met Gly Asp Arg Val Arg Asp Val Ile Glu
                85                  90                  95

Glu Ile Ile Glu Gly Glu Ser Ser Arg Ala Lys Asp Val Leu Asn
            100                 105                 110

Asp Glu Arg Tyr Lys Ser Phe Lys Glu Phe Thr Ser Val Phe Gly Val
        115                 120                 125

Gly Val Lys Thr Ser Glu Lys Trp Phe Arg Met Gly Leu Arg Thr Val
    130                 135                 140

Glu Glu Val Lys Ala Asp Lys Thr Leu Lys Leu Ser Lys Met Gln Arg
145                 150                 155                 160

Ala Gly Phe Leu Tyr Tyr Glu Asp Leu Val Ser Cys Val Ser Lys Ala
                165                 170                 175

Glu Ala Asp Ala Val Ser Ser Ile Val Lys Asn Thr Val Cys Thr Phe
            180                 185                 190

Leu Pro Asp Ala Leu Val Thr Ile Thr Gly Gly Phe Arg Arg Gly Lys
        195                 200                 205

Lys Ile Gly His Asp Ile Asp Phe Leu Ile Thr Ser Pro Gly Gln Arg
    210                 215                 220

Glu Asp Asp Glu Leu Leu His Lys Gly Leu Leu Leu Tyr Cys Asp Ile
225                 230                 235                 240

Ile Glu Ser Thr Phe Val Lys Glu Gln Ile Pro Ser Arg His Val Asp
                245                 250                 255

Ala Met Asp His Phe Gln Lys Cys Phe Ala Ile Leu Lys Leu Tyr Gln
            260                 265                 270
```

```
Pro Arg Val Asp Asn Ser Ser Tyr Asn Met Ser Lys Lys Cys Asp Met
            275                 280                 285

Ala Glu Val Lys Asp Trp Lys Ala Ile Arg Val Asp Leu Val Ile Thr
290                 295                 300

Pro Phe Glu Gln Tyr Ala Tyr Ala Leu Leu Gly Trp Thr Gly Ser Arg
305                 310                 315                 320

Gln Phe Gly Arg Asp Leu Arg Arg Tyr Ala Thr His Glu Arg Lys Met
                325                 330                 335

Met Leu Asp Asn His Ala Leu Tyr Asp Lys Arg Lys Arg Val Phe Leu
            340                 345                 350

Lys Ala Gly Ser Glu Glu Ile Phe Ala His Leu Gly Leu Asp Tyr
355                 360                 365

Val Glu Pro Trp Glu Arg Asn Ala
    370                 375

<210> SEQ ID NO 6
<211> LENGTH: 387
<212> TYPE: PRT
<213> ORGANISM: DIDELPHIS VIRGINIANA

<400> SEQUENCE: 6

Ser Ala Asn Pro Asp Pro Thr Ala Gly Thr Leu Asn Ile Leu Pro Pro
1               5                   10                  15

Thr Thr Lys Thr Ile Ser Gln Tyr Ala Cys Gln Arg Arg Thr Thr Ile
            20                  25                  30

Asn Asn His Asn Gln Arg Phe Thr Asp Ala Phe Glu Ile Leu Ala Lys
        35                  40                  45

Asn Tyr Glu Phe Lys Glu Asn Asp Asp Thr Cys Leu Thr Phe Met Arg
50                  55                  60

Ala Ile Ser Val Leu Lys Cys Leu Pro Phe Glu Val Val Ser Leu Lys
65                  70                  75                  80

Asp Thr Glu Gly Leu Pro Trp Ile Gly Asp Glu Val Lys Gly Ile Met
                85                  90                  95

Glu Glu Ile Ile Glu Asp Gly Glu Ser Leu Glu Val Gln Ala Val Leu
            100                 105                 110

Asn Asp Glu Arg Tyr Gln Ser Phe Lys Leu Phe Thr Ser Val Phe Gly
        115                 120                 125

Val Gly Leu Lys Thr Ala Asp Lys Trp Tyr Arg Met Gly Phe Arg Thr
130                 135                 140

Leu Asn Lys Ile Arg Ser Asp Lys Thr Leu Lys Leu Thr Lys Met Gln
145                 150                 155                 160

Lys Ala Gly Leu Cys Tyr Tyr Glu Asp Leu Ile Asp Cys Val Ser Lys
                165                 170                 175

Ala Glu Ala Asp Ala Val Ser Leu Leu Val Gln Asp Ala Val Trp Thr
            180                 185                 190

Phe Leu Pro Asp Ala Leu Val Thr Ile Thr Gly Gly Phe Arg Arg Gly
        195                 200                 205

Lys Glu Phe Gly His Asp Val Asp Phe Leu Ile Thr Ser Pro Gly Ala
210                 215                 220

Glu Lys Glu Gln Glu Asp Gln Leu Leu Gln Lys Val Thr Asn Leu Trp
225                 230                 235                 240

Lys Lys Gln Gly Leu Leu Leu Tyr Cys Asp Leu Ile Glu Ser Thr Phe
                245                 250                 255

Glu Asp Leu Lys Leu Pro Ser Arg Lys Ile Asp Ala Leu Asp His Phe
            260                 265                 270
```

```
Gln Lys Cys Phe Leu Ile Leu Lys Leu Tyr His His Lys Glu Asp Lys
            275                 280                 285

Arg Lys Trp Glu Met Pro Thr Gly Ser Asn Glu Ser Glu Ala Lys Ser
290                 295                 300

Trp Lys Ala Ile Arg Val Asp Leu Val Val Cys Pro Tyr Asp Arg Tyr
305                 310                 315                 320

Ala Phe Ala Leu Leu Gly Trp Ser Gly Ser Arg Gln Phe Glu Arg Asp
            325                 330                 335

Leu Arg Arg Tyr Ala Thr His Glu Lys Lys Met Met Leu Asp Asn His
            340                 345                 350

Ala Leu Tyr Asp Lys Thr Lys Lys Ile Phe Leu Lys Ala Lys Ser Glu
            355                 360                 365

Glu Glu Ile Phe Ala His Leu Gly Leu Glu Tyr Ile Gln Pro Ser Glu
370                 375                 380

Arg Asn Ala
385

<210> SEQ ID NO 7
<211> LENGTH: 381
<212> TYPE: PRT
<213> ORGANISM: SOREX ARANEUS

<400> SEQUENCE: 7

Asp Cys Pro Ala Ser His Asp Ser Ser Pro Gln Lys Thr Glu Ser Ala
1               5                   10                  15

Ala Val Gln Lys Ile Ser Gln Tyr Ala Cys Gln Arg Arg Thr Thr Leu
            20                  25                  30

Asn Asn His Asn His Ile Phe Thr Asp Ala Phe Glu Ile Leu Ala Glu
        35                  40                  45

Asn Cys Glu Phe Arg Glu Asn Glu Gly Ser Tyr Val Thr Tyr Met Arg
50                  55                  60

Ala Ala Ser Val Leu Lys Ser Leu Pro Phe Ser Ile Ile Ser Met Lys
65                  70                  75                  80

Asp Thr Glu Gly Ile Pro Cys Leu Ala Asp Lys Val Lys Cys Val Ile
                85                  90                  95

Glu Glu Ile Ile Glu Asp Gly Glu Ser Ser Glu Val Lys Ala Val Leu
            100                 105                 110

Asn Asp Glu Arg Tyr Lys Ser Phe Lys Leu Phe Thr Ser Val Phe Gly
        115                 120                 125

Val Gly Leu Lys Thr Ala Glu Lys Trp Phe Arg Leu Gly Phe Arg Thr
130                 135                 140

Leu Ser Gly Ile Met Asn Asp Lys Thr Leu Lys Leu Thr His Met Gln
145                 150                 155                 160

Lys Ala Gly Phe Leu Tyr Tyr Glu Asp Leu Val Ser Cys Val Thr Arg
                165                 170                 175

Ala Glu Ala Glu Ala Val Gly Val Leu Val Lys Glu Ala Val Trp Ala
            180                 185                 190

Phe Leu Pro Asp Ala Ile Val Thr Met Thr Gly Gly Phe Arg Arg Gly
        195                 200                 205

Lys Lys Val Gly His Asp Val Asp Phe Leu Ile Thr Ser Pro Glu Ala
210                 215                 220

Thr Glu Glu Gln Glu Gln Gln Leu Leu His Lys Val Ile Thr Phe Trp
225                 230                 235                 240

Glu Lys Glu Gly Leu Leu Leu Tyr Cys Asp Leu Tyr Glu Ser Thr Phe
```

```
                    245                 250                 255
Glu Lys Leu Lys Met Pro Ser Arg Lys Val Asp Ala Leu Asp His Phe
                260                 265                 270

Gln Lys Cys Phe Leu Ile Leu Lys Leu His Arg Glu Cys Val Asp Asp
            275                 280                 285

Gly Thr Ser Ser Gln Leu Gln Gly Lys Thr Trp Lys Ala Ile Arg Val
        290                 295                 300

Asp Leu Val Val Cys Pro Tyr Glu Cys Arg Ala Phe Ala Leu Leu Gly
305                 310                 315                 320

Trp Thr Gly Ser Pro Gln Phe Glu Arg Asp Leu Arg Arg Tyr Ala Thr
                325                 330                 335

His Glu Arg Lys Met Met Leu Asp Asn His Ala Leu Tyr Asp Lys Thr
            340                 345                 350

Lys Arg Lys Phe Leu Ser Ala Asp Ser Glu Glu Asp Ile Phe Ala His
        355                 360                 365

Leu Gly Leu Asp Tyr Ile Glu Pro Trp Glu Arg Asn Ala
    370                 375                 380

<210> SEQ ID NO 8
<211> LENGTH: 387
<212> TYPE: PRT
<213> ORGANISM: PYTHON BIVITTATUS

<400> SEQUENCE: 8

Glu Lys Tyr Gln Leu Pro Glu Asp Glu Asp Arg Ser Val Thr Ser Asp
1               5                   10                  15

Leu Asp Arg Asp Ser Ile Ser Glu Tyr Ala Cys Gln Arg Arg Thr Thr
                20                  25                  30

Leu Lys Asn Tyr Asn Gln Lys Phe Thr Asp Ala Phe Glu Ile Leu Ala
            35                  40                  45

Glu Asn Tyr Glu Phe Asn Glu Asn Lys Gly Phe Cys Thr Ala Phe Arg
        50                  55                  60

Arg Ala Ala Ser Val Leu Lys Cys Leu Pro Phe Thr Ile Val Gln Val
65                  70                  75                  80

His Asp Ile Glu Gly Val Pro Trp Met Gly Lys Gln Val Lys Gly Ile
                85                  90                  95

Ile Glu Asp Ile Ile Glu Glu Gly Ser Ser Lys Val Lys Ala Val
                100                 105                 110

Leu Asp Asn Glu Asn Tyr Arg Ser Val Lys Leu Phe Thr Ser Val Phe
            115                 120                 125

Gly Val Gly Leu Lys Thr Ser Asp Lys Trp Tyr Arg Met Gly Leu Arg
        130                 135                 140

Thr Leu Glu Glu Val Lys Arg Asp Lys Asn Leu Lys Leu Thr Arg Met
145                 150                 155                 160

Gln Lys Ala Gly Phe Leu His Tyr Asp Asp Leu Thr Ser Cys Val Ser
                165                 170                 175

Lys Ala Glu Ala Asp Ala Ala Ser Leu Ile Val Gln Asp Val Val Trp
            180                 185                 190

Lys Ile Val Pro Asn Ala Ile Val Thr Ile Ala Gly Gly Phe Arg Arg
        195                 200                 205

Gly Lys Gln Thr Gly His Asp Val Asp Phe Leu Ile Thr Val Pro Gly
    210                 215                 220

Ser Lys Gln Glu Glu Glu Glu Leu Leu His Thr Val Ile Asp Ile Trp
225                 230                 235                 240
```

-continued

Lys Lys Gln Glu Leu Leu Tyr Tyr Asp Leu Ile Glu Ser Thr Phe
            245                 250                 255

Glu Asp Thr Lys Leu Pro Ser Arg Lys Val Asp Ala Leu Asp His Phe
        260                 265                 270

Gln Lys Cys Phe Ala Ile Leu Lys Val His Lys Glu Arg Glu Asp Lys
    275                 280                 285

Gly Asn Ser Ile Arg Ser Lys Ala Phe Ser Glu Glu Ile Lys Asp
    290                 295                 300

Trp Lys Ala Ile Arg Val Asp Leu Val Val Pro Phe Glu Gln Tyr
305                 310                 315                 320

Ala Phe Ala Leu Leu Gly Trp Thr Gly Ser Thr Gln Phe Glu Arg Asp
            325                 330                 335

Leu Arg Arg Tyr Ala Thr His Glu Lys Lys Met Met Leu Asp Asn His
            340                 345                 350

Ala Leu Tyr Asp Lys Thr Lys Lys Ile Phe Leu Asn Ala Ala Ser Glu
        355                 360                 365

Glu Glu Ile Phe Ala His Leu Gly Leu Asp Tyr Leu Glu Pro Trp Glu
    370                 375                 380

Arg Asn Ala
385

<210> SEQ ID NO 9
<211> LENGTH: 381
<212> TYPE: PRT
<213> ORGANISM: CANIS LUPUS

<400> SEQUENCE: 9

Asp Tyr Thr Ala Ser Pro Asn Pro Glu Leu Gln Lys Thr Leu Pro Val
1               5                   10                  15

Ala Val Lys Lys Ile Ser Gln Tyr Ala Cys Gln Arg Arg Thr Thr Leu
            20                  25                  30

Asn Asn Tyr Asn Asn Val Phe Thr Asp Ala Phe Glu Val Leu Ala Glu
        35                  40                  45

Asn Tyr Glu Phe Arg Glu Asn Glu Val Phe Ser Leu Thr Phe Met Arg
    50                  55                  60

Ala Ala Ser Val Leu Lys Ser Leu Pro Phe Thr Ile Ile Ser Met Lys
65                  70                  75                  80

Asp Thr Glu Gly Ile Pro Cys Leu Gly Asp Gln Val Lys Cys Ile Ile
                85                  90                  95

Glu Glu Ile Ile Glu Asp Gly Glu Ser Ser Glu Val Lys Ala Val Leu
            100                 105                 110

Asn Asp Glu Arg Tyr Gln Ser Phe Lys Leu Phe Thr Ser Val Phe Gly
        115                 120                 125

Val Gly Leu Lys Thr Ser Glu Lys Trp Phe Arg Met Gly Phe Arg Thr
    130                 135                 140

Leu Ser Lys Ile Lys Ser Asp Lys Ser Leu Lys Phe Thr Pro Met Gln
145                 150                 155                 160

Lys Ala Gly Phe Leu Tyr Tyr Glu Asp Leu Val Ser Cys Val Thr Arg
                165                 170                 175

Ala Glu Ala Glu Ala Val Gly Val Leu Val Lys Glu Ala Val Gly Ala
            180                 185                 190

Phe Leu Pro Asp Ala Phe Val Thr Met Thr Gly Gly Phe Arg Arg Gly
        195                 200                 205

Lys Lys Met Gly His Asp Val Asp Phe Leu Ile Thr Ser Pro Gly Ser
    210                 215                 220

Thr Asp Glu Asp Glu Glu Gln Leu Leu Pro Lys Val Ile Asn Leu Trp
225                 230                 235                 240

Glu Arg Lys Gly Leu Leu Tyr Cys Asp Leu Val Glu Ser Thr Phe
            245                 250                 255

Glu Lys Leu Lys Leu Pro Ser Arg Lys Val Asp Ala Leu Asp His Phe
            260                 265                 270

Gln Lys Cys Phe Leu Ile Leu Lys Leu His His Gln Arg Val Asp Gly
            275                 280                 285

Gly Lys Cys Ser Gln Gln Glu Gly Lys Thr Trp Lys Ala Ile Arg Val
            290                 295                 300

Asp Leu Val Met Cys Pro Tyr Glu Arg Arg Ala Phe Ala Leu Leu Gly
305                 310                 315                 320

Trp Thr Gly Ser Arg Gln Phe Glu Arg Asp Leu Arg Arg Tyr Ala Ser
                325                 330                 335

His Glu Arg Lys Met Ile Leu Asp Asn His Ala Leu Tyr Asp Lys Thr
            340                 345                 350

Lys Lys Ile Phe Leu Lys Ala Glu Ser Glu Glu Ile Phe Ala His
            355                 360                 365

Leu Gly Leu Asp Tyr Ile Glu Pro Trp Glu Arg Asn Ala
    370                 375                 380

<210> SEQ ID NO 10
<211> LENGTH: 382
<212> TYPE: PRT
<213> ORGANISM: SCALOPUS AQUATICUS

<400> SEQUENCE: 10

Gly Asp Cys Pro Ala Ser His Asp Ser Pro Gln Lys Thr Glu Ser
1               5                   10                  15

Ala Ala Val Gln Lys Ile Ser Gln Tyr Ala Cys Gln Arg Arg Thr Thr
            20                  25                  30

Leu Asn Asn His Asn His Ile Phe Thr Asp Ala Phe Glu Ile Leu Ala
            35                  40                  45

Glu Asn Cys Glu Phe Arg Glu Asn Glu Gly Ser Tyr Val Thr Tyr Met
50                  55                  60

Arg Ala Ala Ser Val Leu Lys Ser Leu Pro Phe Ser Ile Ile Ser Met
65                  70                  75                  80

Lys Asp Thr Glu Gly Ile Pro Cys Leu Ala Asp Lys Val Lys Cys Val
                85                  90                  95

Ile Glu Glu Ile Ile Glu Asp Gly Glu Ser Ser Glu Val Lys Ala Val
            100                 105                 110

Leu Asn Asp Glu Arg Tyr Lys Ser Phe Lys Leu Phe Thr Ser Val Phe
            115                 120                 125

Gly Val Gly Leu Lys Thr Ala Glu Lys Trp Phe Arg Leu Gly Phe Arg
            130                 135                 140

Thr Leu Ser Gly Ile Met Asn Asp Lys Thr Leu Lys Leu Thr His Met
145                 150                 155                 160

Gln Lys Ala Gly Phe Leu Tyr Tyr Glu Asp Leu Val Ser Cys Val Thr
                165                 170                 175

Arg Ala Glu Ala Glu Ala Val Gly Val Leu Val Lys Glu Ala Val Trp
            180                 185                 190

Ala Phe Leu Pro Asp Ala Ile Val Thr Met Thr Gly Gly Phe Arg Arg
            195                 200                 205

Gly Lys Lys Val Gly His Asp Val Asp Phe Leu Ile Thr Ser Pro Glu

```
            210                 215                 220
Ala Thr Glu Glu Gln Glu Gln Leu Leu His Lys Val Ile Thr Phe
225                 230                 235                 240

Trp Glu Lys Glu Gly Leu Leu Leu Tyr Cys Asp Leu Tyr Glu Ser Thr
                245                 250                 255

Phe Glu Lys Leu Lys Met Pro Ser Arg Lys Val Asp Ala Leu Asp His
                260                 265                 270

Phe Gln Lys Cys Phe Leu Ile Leu Lys Leu His Arg Glu Cys Val Asp
                275                 280                 285

Asp Gly Thr Ser Ser Gln Leu Gln Gly Lys Thr Trp Lys Ala Ile Arg
        290                 295                 300

Val Asp Leu Val Val Cys Pro Tyr Glu Cys Arg Ala Phe Ala Leu Leu
305                 310                 315                 320

Gly Trp Thr Gly Ser Pro Gln Phe Glu Arg Asp Leu Arg Arg Tyr Ala
                325                 330                 335

Thr His Glu Arg Lys Met Met Leu Asp Asn His Ala Leu Tyr Asp Lys
                340                 345                 350

Thr Lys Arg Lys Phe Leu Ser Ala Asp Ser Glu Glu Asp Ile Phe Ala
                355                 360                 365

His Leu Gly Leu Asp Tyr Ile Glu Pro Trp Glu Arg Asn Ala
        370                 375                 380
```

<210> SEQ ID NO 11
<211> LENGTH: 379
<212> TYPE: PRT
<213> ORGANISM: OCHOTONA PRINCEPS

<400> SEQUENCE: 11

```
Glu Tyr Ser Ala Asn Pro Ser Pro Gly Pro Gln Ala Thr Pro Ala Val
1               5                   10                  15

Tyr Lys Ile Ser Gln Tyr Ala Cys Gln Arg Thr Thr Leu Asn Asn
                20                  25                  30

His Asn His Ile Phe Thr Asp Ala Phe Glu Ile Leu Ala Glu Asn Tyr
        35                  40                  45

Glu Phe Lys Glu Asn Glu Gly Cys Tyr Val Thr Tyr Met Arg Ala Ala
    50                  55                  60

Ser Val Leu Lys Ser Leu Pro Phe Thr Ile Val Ser Met Lys Asp Thr
65                  70                  75                  80

Glu Gly Ile Pro Cys Leu Glu Asp Lys Val Lys Ser Ile Met Glu Glu
                85                  90                  95

Ile Ile Glu Glu Gly Glu Ser Ser Glu Val Lys Ala Val Leu Ser Asp
                100                 105                 110

Glu Arg Tyr Gln Cys Phe Lys Leu Phe Thr Ser Val Phe Gly Val Gly
        115                 120                 125

Leu Lys Thr Ser Glu Lys Trp Phe Arg Met Gly Phe Arg Ser Leu Ser
130                 135                 140

Asn Ile Arg Leu Asp Lys Ser Leu Lys Phe Thr Gln Met Gln Lys Ala
145                 150                 155                 160

Gly Phe Arg Tyr Tyr Glu Asp Ile Val Ser Cys Val Thr Arg Ala Glu
                165                 170                 175

Ala Glu Ala Val Asp Val Leu Val Asn Glu Ala Val Arg Ala Phe Leu
                180                 185                 190

Pro Asp Ala Phe Ile Thr Met Thr Gly Gly Phe Arg Arg Gly Lys Lys
            195                 200                 205
```

```
Ile Gly His Asp Val Asp Phe Leu Ile Thr Ser Pro Glu Leu Thr Glu
210                 215                 220

Glu Asp Glu Gln Gln Leu Leu His Lys Val Met Asn Leu Trp Glu Lys
225                 230                 235                 240

Lys Gly Leu Leu Leu Tyr His Asp Leu Val Glu Ser Thr Phe Glu Lys
            245                 250                 255

Leu Lys Gln Pro Ser Arg Lys Val Asp Ala Leu Asp His Phe Gln Lys
        260                 265                 270

Cys Phe Leu Ile Phe Lys Leu Tyr His Glu Arg Val Gly Gly Asp Arg
    275                 280                 285

Cys Arg Gln Pro Glu Gly Lys Asp Trp Lys Ala Ile Arg Val Asp Leu
290                 295                 300

Val Met Cys Pro Tyr Glu Cys His Ala Phe Ala Leu Leu Gly Trp Thr
305                 310                 315                 320

Gly Ser Arg Gln Phe Glu Arg Asp Leu Arg Arg Tyr Ala Ser His Glu
                325                 330                 335

Arg Lys Met Ile Leu Asp Asn His Ala Leu Tyr Asp Lys Thr Lys Arg
            340                 345                 350

Val Phe Leu Gln Ala Glu Asn Glu Glu Ile Phe Ala His Leu Gly
        355                 360                 365

Leu Asp Tyr Ile Glu Pro Trp Glu Arg Asn Ala
370                 375

<210> SEQ ID NO 12
<211> LENGTH: 384
<212> TYPE: PRT
<213> ORGANISM: ERINACEUS EUROPAEUS

<400> SEQUENCE: 12

Asp Ala Ser Phe Gly Ser Asn Pro Gly Ser Gln Asn Thr Pro Pro Leu
1               5                   10                  15

Ala Ile Lys Lys Ile Ser Gln Tyr Ala Cys Gln Arg Arg Thr Ser Leu
            20                  25                  30

Asn Asn Cys Asn His Ile Phe Thr Asp Ala Leu Asp Ile Leu Ala Glu
        35                  40                  45

Asn His Glu Phe Arg Glu Asn Glu Val Ser Cys Val Ala Phe Met Arg
    50                  55                  60

Ala Ala Ser Val Leu Lys Ser Leu Pro Phe Thr Ile Ile Ser Met Lys
65                  70                  75                  80

Asp Thr Lys Gly Ile Pro Cys Leu Gly Asp Lys Ala Lys Cys Val Ile
                85                  90                  95

Glu Glu Ile Ile Glu Asp Gly Glu Ser Ser Glu Val Lys Ala Ile Leu
            100                 105                 110

Asn Asp Glu Arg Tyr Gln Ser Phe Lys Leu Phe Thr Ser Val Phe Gly
        115                 120                 125

Val Gly Leu Lys Thr Ser Glu Lys Trp Phe Arg Met Gly Phe Arg Thr
    130                 135                 140

Leu Asn Lys Ile Met Ser Asp Lys Thr Leu Lys Leu Thr Arg Met Gln
145                 150                 155                 160

Lys Ala Gly Phe Leu Tyr Tyr Glu Asp Leu Val Ser Cys Val Ala Lys
                165                 170                 175

Ala Glu Ala Asp Ala Val Ser Val Leu Val Gln Glu Ala Val Trp Ala
            180                 185                 190

Phe Leu Pro Asp Ala Met Val Thr Met Thr Gly Gly Phe Arg Arg Gly
        195                 200                 205
```

```
Lys Lys Leu Gly His Asp Val Asp Phe Leu Ile Thr Ser Pro Gly Ala
210                 215                 220

Thr Glu Glu Glu Glu Gln Leu Leu Pro Lys Val Ile Asn Phe Trp
225                 230                 235                 240

Glu Arg Lys Gly Leu Leu Leu Tyr His Asp Leu Val Glu Ser Thr Phe
                245                 250                 255

Glu Lys Leu Lys Leu Pro Ser Arg Lys Val Asp Ala Leu Asp His Phe
            260                 265                 270

Gln Lys Cys Phe Leu Ile Leu Lys Leu His Leu Gln His Val Asn Gly
        275                 280                 285

Val Gly Asn Ser Lys Thr Gly Gln Gln Glu Gly Lys Asn Trp Lys Ala
290                 295                 300

Ile Arg Val Asp Leu Val Met Cys Pro Tyr Glu Arg Arg Ala Phe Ala
305                 310                 315                 320

Leu Leu Gly Trp Thr Gly Ser Arg Gln Phe Glu Arg Asp Leu Arg Arg
                325                 330                 335

Phe Ala Thr His Glu Arg Lys Met Met Leu Asp Asn His Ala Leu Tyr
            340                 345                 350

Asp Lys Thr Lys Arg Ile Phe Leu Lys Ala Glu Ser Glu Glu Glu Ile
        355                 360                 365

Phe Ala His Leu Gly Leu Asp Tyr Ile Asp Pro Trp Glu Arg Asn Ala
370                 375                 380

<210> SEQ ID NO 13
<211> LENGTH: 381
<212> TYPE: PRT
<213> ORGANISM: TUPAIA BELANGERI

<400> SEQUENCE: 13

Asp His Ser Thr Ser Pro Ser Pro Gly Pro Gln Lys Thr Pro Ala Leu
1               5                   10                  15

Ala Val Gln Lys Ile Ser Gln Tyr Ala Cys Gln Arg Arg Thr Thr Leu
                20                  25                  30

Asn Asn Cys Asn Arg Val Phe Thr Asp Ala Phe Glu Thr Leu Ala Glu
            35                  40                  45

Asn Tyr Glu Phe Arg Glu Asn Glu Asp Ser Ser Val Ile Phe Leu Arg
        50                  55                  60

Ala Ala Ser Val Leu Arg Ser Leu Pro Phe Thr Ile Thr Ser Met Arg
65                  70                  75                  80

Asp Thr Glu Gly Leu Pro Cys Leu Gly Asp Lys Val Lys Cys Val Ile
                85                  90                  95

Glu Glu Ile Ile Glu Asp Gly Glu Ser Ser Glu Val Asn Ala Val Leu
                100                 105                 110

Asn Asp Glu Arg Tyr Lys Ser Phe Lys Leu Phe Thr Ser Val Phe Gly
            115                 120                 125

Val Gly Leu Lys Thr Ser Glu Lys Trp Phe Arg Met Gly Phe Arg Thr
130                 135                 140

Leu Ser Arg Val Arg Ser Asp Lys Ser Leu His Leu Thr Arg Met Gln
145                 150                 155                 160

Gln Ala Gly Phe Leu Tyr Tyr Glu Asp Leu Ala Ser Cys Val Thr Arg
                165                 170                 175

Ala Glu Ala Glu Ala Val Gly Val Leu Val Lys Glu Ala Val Gly Ala
            180                 185                 190

Phe Leu Pro Asp Ala Leu Val Thr Ile Thr Gly Gly Phe Arg Arg Gly
```

```
              195                 200                 205
Lys Lys Thr Gly His Asp Val Asp Phe Leu Ile Thr Ser Pro Gly Ser
    210                 215                 220

Thr Glu Glu Lys Glu Glu Leu Leu Gln Lys Val Leu Asn Leu Trp
225                 230                 235                 240

Glu Lys Lys Gly Leu Leu Tyr Tyr Asp Leu Val Glu Ser Thr Phe
                245                 250                 255

Glu Lys Leu Lys Thr Pro Ser Arg Lys Val Asp Ala Leu Asp His Phe
            260                 265                 270

Pro Lys Cys Phe Leu Ile Leu Lys Leu His His Gln Arg Val Asp Gly
                275                 280                 285

Asp Lys Pro Ser Gln Gln Glu Gly Lys Ser Trp Lys Ala Ile Arg Val
    290                 295                 300

Asp Leu Val Met Cys Pro Tyr Glu Arg His Ala Phe Ala Leu Leu Gly
305                 310                 315                 320

Trp Thr Gly Ser Arg Gln Phe Glu Arg Asp Leu Arg Arg Tyr Ala Thr
                325                 330                 335

His Glu Arg Lys Met Met Leu Asp Asn His Ala Leu Tyr Asp Lys Thr
                340                 345                 350

Lys Arg Val Phe Leu Lys Ala Glu Ser Glu Glu Asp Ile Phe Ala His
                355                 360                 365

Leu Gly Leu Asp Tyr Ile Glu Pro Trp Glu Arg Asn Ala
370                 375                 380

<210> SEQ ID NO 14
<211> LENGTH: 394
<212> TYPE: PRT
<213> ORGANISM: ORNITHORHYNCHUS ANATINUS

<400> SEQUENCE: 14

Leu Thr Asn Ser Ala Pro Ile Asn Cys Met Thr Glu Thr Pro Ser Leu
1               5                   10                  15

Ala Thr Lys Gln Val Ser Gln Tyr Ala Cys Glu Arg Arg Thr Thr Leu
                20                  25                  30

Asn Asn Cys Asn Gln Lys Phe Thr Asp Ala Phe Glu Ile Leu Ala Lys
            35                  40                  45

Asp Phe Glu Phe Arg Glu Asn Glu Gly Ile Cys Leu Ala Phe Met Arg
    50                  55                  60

Ala Ile Ser Val Leu Lys Cys Leu Pro Phe Thr Ile Val Arg Met Lys
65                  70                  75                  80

Asp Ile Glu Gly Val Pro Trp Leu Gly Asp Gln Val Lys Ser Ile Ile
                85                  90                  95

Glu Glu Ile Ile Glu Asp Gly Glu Ser Ser Val Lys Ala Val Leu
            100                 105                 110

Asn Asp Glu Arg Tyr Arg Ser Phe Gln Leu Phe Asn Ser Val Phe Glu
    115                 120                 125

Val Gly Leu Thr Asp Asn Gly Glu Asn Gly Ile Ala Arg Gly Phe Gln
130                 135                 140

Thr Leu Asn Glu Val Ile Thr Asp Glu Asn Ile Ser Leu Thr Lys Thr
145                 150                 155                 160

Thr Leu Ser Thr Ser Leu Trp Asn Tyr Leu Pro Gly Phe Leu Tyr Tyr
                165                 170                 175

Glu Asp Leu Val Ser Cys Val Ala Lys Glu Glu Ala Asp Ala Val Tyr
            180                 185                 190
```

```
Leu Ile Val Lys Glu Ala Val Arg Ala Phe Leu Pro Glu Ala Leu Val
            195                 200                 205

Thr Leu Thr Gly Gly Phe Arg Arg Gly Lys Lys Ile Gly His Asp Val
    210                 215                 220

Asp Phe Leu Ile Ser Asp Pro Glu Ser Gly Gln Asp Glu Gln Leu Leu
225                 230                 235                 240

Pro Asn Ile Ile Lys Leu Trp Glu Lys Gln Glu Leu Leu Leu Tyr Tyr
                245                 250                 255

Asp Leu Val Glu Ser Thr Phe Glu Lys Thr Lys Ile Pro Ser Arg Lys
                260                 265                 270

Val Asp Ala Met Asp His Phe Gln Lys Cys Phe Leu Ile Leu Lys Leu
                275                 280                 285

His His Gln Lys Val Asp Ser Gly Arg Tyr Lys Pro Pro Glu Ser
    290                 295                 300

Lys Asn His Glu Ala Lys Asn Trp Lys Ala Ile Arg Val Asp Leu Val
305                 310                 315                 320

Met Cys Pro Phe Glu Gln Tyr Ala Tyr Ala Leu Leu Gly Trp Thr Gly
                325                 330                 335

Ser Arg Gln Phe Glu Arg Asp Leu Arg Arg Tyr Ala Thr His Glu Lys
                340                 345                 350

Lys Met Met Leu Asp Asn His Ala Leu Tyr Asp Lys Thr Lys Lys Ile
                355                 360                 365

Phe Leu Lys Ala Glu Ser Glu Glu Asp Ile Phe Thr His Leu Gly Leu
                370                 375                 380

Asp Tyr Ile Glu Pro Trp Glu Arg Asn Ala
385                 390

<210> SEQ ID NO 15
<211> LENGTH: 384
<212> TYPE: PRT
<213> ORGANISM: JACULUS JACULUS

<400> SEQUENCE: 15

Ser Ser Glu Leu Glu Leu Leu Asp Val Ser Trp Leu Ile Glu Cys Met
1               5                   10                  15

Gly Ala Gly Lys Pro Val Glu Met Thr Gly Arg His Gln Leu Val Lys
                20                  25                  30

Gln Thr Phe Cys Leu Pro Gly Phe Ile Leu Gln Asp Ala Phe Asp Ile
            35                  40                  45

Leu Ala Glu Asn Cys Glu Phe Arg Glu Asn Glu Ala Ser Cys Val Glu
        50                  55                  60

Phe Met Arg Ala Ala Ser Val Leu Lys Ser Leu Pro Phe Pro Ile Ile
65                  70                  75                  80

Ser Val Lys Asp Thr Glu Gly Ile Pro Trp Leu Gly Gly Lys Val Lys
                85                  90                  95

Cys Val Ile Glu Glu Ile Ile Glu Asp Gly Glu Ser Ser Glu Val Lys
            100                 105                 110

Ala Leu Leu Asn Asp Glu Arg Tyr Lys Ser Phe Lys Leu Phe Thr Ser
        115                 120                 125

Val Phe Gly Val Gly Leu Lys Thr Ala Glu Arg Trp Phe Arg Met Gly
    130                 135                 140

Phe Arg Thr Leu Ser Thr Val Lys Leu Asp Lys Ser Leu Thr Phe Thr
145                 150                 155                 160

Arg Met Gln Lys Ala Gly Phe Leu His Tyr Glu Asp Leu Val Ser Cys
                165                 170                 175
```

-continued

```
Val Thr Arg Ala Glu Ala Glu Ala Val Ser Val Leu Val Gln Gln Ala
            180                 185                 190

Val Val Ala Phe Leu Pro Asp Ala Leu Val Ser Met Thr Gly Gly Phe
        195                 200                 205

Arg Arg Gly Lys Lys Ile Gly His Asp Val Asp Phe Leu Ile Thr Ser
    210                 215                 220

Pro Glu Ala Thr Glu Glu Glu Gln Gln Leu Leu His Lys Val Thr
225                 230                 235                 240

Asn Phe Trp Glu Gln Lys Gly Leu Leu Leu Tyr Cys Asp His Val Glu
                245                 250                 255

Ser Thr Phe Glu Lys Cys Lys Leu Pro Ser Arg Lys Val Asp Ala Leu
            260                 265                 270

Asp His Phe Gln Lys Cys Phe Leu Ile Leu Lys Leu Tyr Arg Glu Arg
        275                 280                 285

Val Asp Ser Val Lys Ser Ser Gln Gln Glu Gly Lys Gly Trp Lys Ala
    290                 295                 300

Ile Arg Val Asp Leu Val Met Cys Pro Tyr Glu Cys Arg Ala Phe Ala
305                 310                 315                 320

Leu Leu Gly Trp Thr Gly Ser Arg Gln Phe Glu Arg Asp Leu Arg Arg
                325                 330                 335

Tyr Ala Thr His Glu Arg Lys Met Arg Leu Asp Asn His Ala Leu Tyr
            340                 345                 350

Asp Lys Thr Lys Arg Val Phe Leu Lys Ala Glu Ser Glu Glu Glu Ile
        355                 360                 365

Phe Ala His Leu Gly Leu Glu Tyr Ile Glu Pro Leu Glu Arg Asn Ala
    370                 375                 380
```